US008712519B1

(12) United States Patent
Panescu et al.

(10) Patent No.: US 8,712,519 B1
(45) Date of Patent: Apr. 29, 2014

(54) CLOSED-LOOP ADAPTIVE ADJUSTMENT OF PACING THERAPY BASED ON CARDIOGENIC IMPEDANCE SIGNALS DETECTED BY AN IMPLANTABLE MEDICAL DEVICE

(75) Inventors: Dorin Panescu, San Jose, CA (US); Weiqun Yang, Cupertino, CA (US); Louis Wong, Sunnyvale, CA (US); Nils Holmstrom, Jarfalla (SE); Andre Walker, Monte Sereno, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 1257 days.

(21) Appl. No.: 11/558,194

(22) Filed: Nov. 9, 2006

Related U.S. Application Data

(63) Continuation-in-part of application No. 11/558,101, filed on Nov. 9, 2006.

(60) Provisional application No. 60/787,884, filed on Mar. 31, 2006.

(51) Int. Cl.
*A61N 1/365* (2006.01)

(52) U.S. Cl.
CPC ................................. *A61N 1/36521* (2013.01)
USPC .................................................. 607/9; 607/18

(58) Field of Classification Search
CPC ................................................. A61N 1/36521
USPC ............. 607/2, 6, 7, 11, 17, 18, 20, 23, 28, 9; 600/547
See application file for complete search history.

(56) References Cited

U.S. PATENT DOCUMENTS

| 3,934,458 | A | 1/1976 | Beretsky |
| 4,535,774 | A | 8/1985 | Olson |
| 4,686,987 | A | 8/1987 | Salo et al. |

(Continued)

FOREIGN PATENT DOCUMENTS

| WO | WO 96/15827 | 5/1996 |
| WO | WO 96/19260 | 6/1996 |

(Continued)

OTHER PUBLICATIONS

Non-Final Office Action mailed Jun. 10, 2009: Related U.S. Appl. No. 11/684,677.

(Continued)

*Primary Examiner* — Allen Porter, Jr.
(74) *Attorney, Agent, or Firm* — Steven M. Mitchell

(57) ABSTRACT

Techniques are provided for controlling therapy provided by the implantable cardiac stimulation device based on cardiogenic impedance. A cardiogenic impedance signal (or intracardiac impedance signal) is an impedance signal representative of the beating of the heart of the patient in which the device is implanted. The cardiogenic impedance signal is sensed along a sensing vector passing through at least a portion of the heart so that the sensed impedance is affected by the mechanical beating of the heart along that sensing vector. Pacing therapy is automatically and adaptively adjusted based on the cardiogenic impedance signal. For example, pacing timing parameters such as the atrioventricular delay and the inter-ventricular delay may be adjusted. Preferably, the adjustments are adaptive, i.e. the adjustments are performed in a closed-loop so as to adapt the adjustments to changes in the cardiogenic impedance signal so as to optimize therapy. In one particular example, the adjustments are performed so as to reduce a degree of fractionation within a cardiogenic impedance waveform.

50 Claims, 15 Drawing Sheets

(56) References Cited

U.S. PATENT DOCUMENTS

| | | | |
|---|---|---|---|
| 5,003,976 A * | 4/1991 | Alt | 607/18 |
| 5,042,303 A | 8/1991 | Geluk | |
| 5,133,365 A * | 7/1992 | Heil et al. | 607/122 |
| 5,154,171 A * | 10/1992 | Chirife | 607/24 |
| 5,178,151 A | 1/1993 | Sackner | |
| 5,179,946 A | 1/1993 | Weiss | |
| 5,190,035 A | 3/1993 | Salo et al. | |
| 5,201,865 A | 4/1993 | Kuehn | |
| 5,282,840 A | 2/1994 | Hudrlik | |
| 5,300,093 A | 4/1994 | Koestner et al. | |
| 5,334,222 A | 8/1994 | Salo | |
| 5,417,717 A | 5/1995 | Salo | |
| 5,427,112 A * | 6/1995 | Noren et al. | 600/515 |
| 5,441,523 A | 8/1995 | Nappholz | |
| 5,476,483 A | 12/1995 | Bornzin | |
| 5,487,752 A | 1/1996 | Salo | |
| 5,507,785 A | 4/1996 | Deno | |
| 5,531,772 A | 7/1996 | Prutchi | |
| 5,549,642 A * | 8/1996 | Min et al. | 607/5 |
| 5,584,868 A | 12/1996 | Salo | |
| 5,609,610 A | 3/1997 | Nappholz | |
| 5,615,684 A | 4/1997 | Hagel et al. | |
| 5,676,141 A | 10/1997 | Hollub | |
| 5,690,687 A | 11/1997 | Hansen | |
| 5,713,935 A | 2/1998 | Prutchi | |
| 5,800,467 A | 9/1998 | Park et al. | |
| 5,814,088 A | 9/1998 | Paul | |
| 5,957,861 A | 9/1999 | Combs | |
| 5,974,340 A * | 10/1999 | Kadhiresan | 607/18 |
| 6,044,297 A | 3/2000 | Sheldon | |
| 6,073,049 A | 6/2000 | Alt | |
| 6,104,949 A * | 8/2000 | Pitts Crick et al. | 600/547 |
| 6,198,965 B1 | 3/2001 | Penner | |
| 6,219,579 B1 | 4/2001 | Bakels | |
| 6,223,082 B1 | 4/2001 | Bakels | |
| 6,233,485 B1 | 5/2001 | Armstrong | |
| 6,249,705 B1 | 6/2001 | Snell | |
| 6,251,303 B1 | 6/2001 | Bawendi | |
| 6,275,727 B1 | 8/2001 | Hopper et al. | |
| 6,278,894 B1 | 8/2001 | Salo et al. | |
| 6,285,907 B1 | 9/2001 | Kramer | |
| 6,337,994 B1 | 1/2002 | Stoianovici | |
| 6,411,848 B2 | 6/2002 | Kramer | |
| 6,438,408 B1 | 8/2002 | Mulligan | |
| 6,459,929 B1 | 10/2002 | Hopper et al. | |
| 6,473,647 B1 | 10/2002 | Bradley | |
| 6,480,733 B1 | 11/2002 | Turcott | |
| 6,501,983 B1 | 12/2002 | Natarajan | |
| 6,510,343 B2 | 1/2003 | Armstrong | |
| 6,512,949 B1 | 1/2003 | Combs et al. | |
| 6,512,952 B2 | 1/2003 | Stahmann | |
| 6,522,923 B1 | 2/2003 | Turcott | |
| 6,527,729 B1 | 3/2003 | Turcott | |
| 6,539,261 B2 | 3/2003 | Dal Molin | |
| 6,553,259 B2 | 4/2003 | Mouchawar | |
| 6,572,557 B2 | 6/2003 | Tchou et al. | |
| 6,575,912 B1 | 6/2003 | Turcott | |
| 6,595,927 B2 | 7/2003 | Pitts-Crick et al. | |
| 6,620,186 B2 | 9/2003 | Saphon | |
| 6,628,988 B2 | 9/2003 | Kramer et al. | |
| 6,641,542 B2 | 11/2003 | Cho | |
| 6,643,546 B2 | 11/2003 | Mathis | |
| 6,643,548 B1 | 11/2003 | Mai et al. | |
| 6,645,153 B2 | 11/2003 | Kroll | |
| 6,708,061 B2 | 3/2004 | Salo | |
| 6,741,885 B1 | 5/2004 | Park et al. | |
| 6,748,261 B1 | 6/2004 | Kroll | |
| 6,751,503 B1 * | 6/2004 | Kroll | 607/18 |
| 6,754,530 B2 | 6/2004 | Bakels | |
| 6,823,215 B2 | 11/2004 | Obel | |
| 6,847,843 B1 | 1/2005 | Mouchawar | |
| 6,920,356 B2 | 7/2005 | Armstrong | |
| 6,961,615 B2 | 11/2005 | Kroll | |
| 6,970,742 B2 | 11/2005 | Mann | |
| 7,065,403 B1 | 6/2006 | Mouchawar | |
| 7,130,689 B1 * | 10/2006 | Turcott | 607/27 |
| 7,200,442 B1 | 4/2007 | Koh | |
| 7,272,443 B2 * | 9/2007 | Min et al. | 607/17 |
| 7,410,467 B2 | 8/2008 | Cooper | |
| 2001/0010009 A1 * | 7/2001 | Bakels et al. | 607/9 |
| 2001/0012953 A1 * | 8/2001 | Molin et al. | 607/9 |
| 2001/0037067 A1 * | 11/2001 | Tchou et al. | 600/483 |
| 2001/0051774 A1 | 12/2001 | Littrup | |
| 2002/0002389 A1 | 1/2002 | Bradley | |
| 2003/0074029 A1 * | 4/2003 | Deno et al. | 607/23 |
| 2003/0083712 A1 | 5/2003 | Rueter | |
| 2003/0220556 A1 | 11/2003 | Porat | |
| 2004/0015196 A1 | 1/2004 | Holmstrom | |
| 2004/0049235 A1 * | 3/2004 | Deno et al. | 607/9 |
| 2004/0049238 A1 * | 3/2004 | Jarverud | 607/17 |
| 2004/0059220 A1 | 3/2004 | Mourad | |
| 2004/0064161 A1 | 4/2004 | Gunderson | |
| 2004/0215097 A1 | 10/2004 | Wang | |
| 2004/0220640 A1 | 11/2004 | Burnes | |
| 2004/0230112 A1 | 11/2004 | Scholz | |
| 2005/0124908 A1 | 6/2005 | Belalcazar | |
| 2005/0182447 A1 * | 8/2005 | Schecter | 607/2 |
| 2005/0215914 A1 * | 9/2005 | Bornzin et al. | 600/508 |
| 2005/0216067 A1 * | 9/2005 | Min et al. | 607/17 |
| 2005/0283091 A1 | 12/2005 | Kink | |
| 2006/0025828 A1 | 2/2006 | Armstrong | |
| 2006/0129196 A1 | 6/2006 | Dong | |
| 2006/0135886 A1 | 6/2006 | Lippert | |
| 2006/0184060 A1 | 8/2006 | Belalcazar | |
| 2006/0235480 A1 | 10/2006 | Schecter | |
| 2006/0241512 A1 | 10/2006 | Kwok | |
| 2006/0247702 A1 * | 11/2006 | Stegemann et al. | 607/17 |
| 2006/0293609 A1 | 12/2006 | Stahmann | |
| 2006/0293714 A1 * | 12/2006 | Salo et al. | 607/9 |
| 2007/0005114 A1 * | 1/2007 | Salo et al. | 607/17 |
| 2008/0221477 A1 | 9/2008 | Olson | |

FOREIGN PATENT DOCUMENTS

| | | |
|---|---|---|
| WO | WO 98/07467 | 2/1998 |
| WO | 0113792 A1 | 3/2001 |
| WO | 0132260 A1 | 5/2001 |
| WO | WO 01/87410 A2 | 11/2001 |
| WO | WO 01/87410 A3 | 11/2001 |
| WO | 2004096041 A2 | 11/2004 |
| WO | 2004096041 A3 | 11/2004 |
| WO | WO2004105862 | 12/2004 |

OTHER PUBLICATIONS

Non-Final Office Action mailed May 27, 2009: Related U.S. Appl. No. 11/684,681.

Non-Final Office Action mailed Apr. 6, 2009: Related U.S. Appl. No. 11/558,101.

Non-Final Office Action mailed Feb. 3, 2009: Related U.S. Appl. No. 11/557,851.

Non-Final Office Action mailed May 29, 2009: Related U.S. Appl. No. 11/557,870.

Non-Final Office Action mailed Jun. 10, 2009: Related U.S. Appl. No. 11/557,882.

Non-Final Office Action mailed Jun. 19, 2009 Related U.S. Appl. No. 11/684,664.

Non-Final Office Action mailed Jun. 22, 2009 Related U.S. Appl. No. 11/684,670.

Non-Final Office Action mailed Jun. 23, 2009 Related U.S. Appl. No. 11/558,088.

Final Office Action mailed Oct. 8, 2009: Related U.S. Appl. No. 11/558,101.

* cited by examiner

CLOSED-LOOP ADAPTIVE ADJUSTMENT OF PACING THERAPY BASED ON CARDIOGENIC IMPEDANCE SIGNALS DETECTED BY AN IMPLANTABLE MEDICAL DEVICE

RELATED APPLICATIONS

This application is related to U.S. Provisional Patent Application No. 60/787,884 of Wong et al., entitled, "Tissue Characterization Using Intracardiac Impedances with an Implantable Lead System," filed Mar. 31, 2006 and is also related to U.S. patent application Ser. No. 11/558,101, filed Nov. 9, 2006, Ser. No. 11/557,851, filed Nov. 8, 2006, Ser. No. 11/557,870, filed Nov. 8, 2006, Ser. No. 11/557,882 filed Nov. 8, 2006, and Ser. No. 11/558,088, filed Nov. 9, 2006, each entitled "Systems and Methods to Monitor and Treat Heart Failure Conditions", of Panescu et al. Each of the foregoing applications is fully incorporated by reference herein, including the appendices thereof. This application claims priority on U.S. patent application Ser. No. 11/558,101, filed Nov. 9, 2006, as a Continuation-in-Part (CIP) thereof.

FIELD OF THE INVENTION

The invention relates generally to implantable medical devices such as pacemakers and implantable cardioverter defibrillators (ICDs) and in particular to techniques for controlling pacing therapy applied to the heart, such as cardiac resynchronization therapy (CRT) applied to alleviate heart failure and related conditions.

BACKGROUND OF THE INVENTION

Heart failure is a debilitating disease in which abnormal function of the heart leads to inadequate blood flow to fulfill the needs of the tissues and organs of the body. Typically, the heart loses propulsive power because the cardiac muscle loses capacity to stretch and contract. Often, the ventricles do not adequately fill with blood between heartbeats and the valves regulating blood flow become leaky, allowing regurgitation or back-flow of blood. The impairment of arterial circulation deprives vital organs of oxygen and nutrients. Fatigue, weakness and the inability to carry out daily tasks may result. Not all heart failure patients suffer debilitating symptoms immediately. Some may live actively for years. Yet, with few exceptions, the disease is relentlessly progressive. As heart failure progresses, it tends to become increasingly difficult to manage. Even the compensatory responses it triggers in the body may themselves eventually complicate the clinical prognosis. For example, when the heart attempts to compensate for reduced cardiac output, it adds cardiac muscle causing the ventricles to grow in volume in an attempt to pump more blood with each heartbeat, i.e. to increase the stroke volume. This places a still higher demand on the heart's oxygen supply. If the oxygen supply falls short of the growing demand, as it often does, further injury to the heart may result, typically in the form of myocardial ischemia or myocardial infarction. The additional muscle mass may also stiffen the heart walls to hamper rather than assist in providing cardiac output. A particularly severe form of heart failure is congestive heart failure (CHF) wherein the weak pumping of the heart leads to build-up of fluids in the lungs and other organs and tissues.

One particular technique for addressing heart failure is CRT, which seeks to normalize asynchronous cardiac electrical activation and the resultant asynchronous contractions by delivering synchronized pacing stimulus to the ventricles using pacemakers or ICDs equipped with biventricular pacing capability. The pacing stimulus is typically synchronized so as to help to improve overall cardiac function. This may have the additional beneficial effect of reducing the susceptibility to life-threatening tachyarrhythmias. With CRT, pacing pulses are selectively delivered to the left and right ventricles in an attempt to ensure that the ventricles contract more uniformly. CRT may also be employed for patients whose nerve conduction pathways are corrupted due, e.g., to right bundle branch block or due to other problems such as the development of scar tissue within the myocardium following a myocardial infarction. CRT and related therapies are discussed in, for example, U.S. Pat. No. 6,643,546 to Mathis, et al., entitled "Multi-Electrode Apparatus And Method For Treatment Of Congestive Heart Failure"; U.S. Pat. No. 6,628,988 to Kramer, et al., entitled "Apparatus And Method For Reversal Of Myocardial Remodeling With Electrical Stimulation"; and U.S. Pat. No. 6,512,952 to Stahmann, et al., entitled "Method And Apparatus For Maintaining Synchronized Pacing".

Although CRT and related techniques have been found to be effective in mitigating problems arising due to heart failure or other conditions, considerable room for improvement remains. Typically, CRT is performed so as to improve some measure of cardiac performance such as cardiac output or stroke volume. Ideally, the CRT parameters would be adjusted in real-time so as to respond automatically to changes in cardiac performance. This however would typically require that cardiac performance be continuously evaluated, which is impractical. Accordingly, it would be desirable to provide more efficient techniques for automatically adjusting CRT pacing parameters or other pacing therapy parameters. It is to that end that the invention is primarily directed.

SUMMARY OF THE INVENTION

In accordance with an exemplary embodiment, a method is provided for controlling therapy provided by an implantable cardiac stimulation device based on cardiogenic impedance. The method comprises detecting a cardiogenic impedance signal ($Z_C$) and adjusting therapy provided by the device based on the cardiogenic impedance signal ($Z_C$). A cardiogenic impedance signal (or intracardiac impedance signal) is an impedance signal representative of the beating of the heart of the patient in which the device is implanted. Typically, the cardiogenic impedance signal is sensed along a sensing vector passing through at least a portion of the heart so that the sensed impedance is affected by the mechanical beating of the heart along that sensing vector. Multiple cardiogenic impedance signals may be sensed using different sensing vectors each passing through different portions of the heart so as to be representative of the beating of different chambers of the heart or different portions of the myocardium. Typically, the therapy to be adjusted is pacing therapy. For example, pacing timing parameters such as the atrioventricular (AV) delay and the inter-ventricular (LV-RV) delay may be adjusted, wherein LV refers to the left ventricle and RV refers to the right ventricle. Within systems equipped to provide pacing at different locations within the same chamber, intra-ventricular ($LV_1$-$LV_2$) or intra-atrial ($LA_1$-$LA_2$) delay values may additionally or alternatively be adjusted. Preferably, the adjustments are adaptive, i.e. the adjustments are performed in a closed-loop so as to adapt the adjustments to changes in the cardiogenic impedance signal so as to optimize therapy.

By adjusting pacing parameters based on one or more cardiogenic impedance signals, the parameters can be promptly adjusted to immediately respond to changes within the heart, such as any deterioration in mechanical synchrony arising due to CHF, conduction defects or other ailments such as myocardial infarction or acute cardiac ischemia. Moreover, by adaptively adjusting the pacing parameters based on cardiogenic impedance, the direction and/or magnitude of the adjustments need not be pre-determined. That is, it need not be known in advance whether a particular pacing parameter should be increased or decreased in response to a deterioration in inter-ventricular mechanical synchrony. Adaptive adjustment allows the direction and magnitude of any adjustments to the pacing parameters to be automatically optimized. Thus, if an initial increase in a particular pacing parameter causes a further deterioration in mechanical synchrony, the pacing parameter may then be automatically decreased in an attempt to improve synchrony. If neither an increase nor a decrease in a particular pacing parameter significantly affects mechanical synchrony, then a different pacing parameter may be selected for adaptive adjustment.

In an illustrative embodiment, the device analyzes the cardiogenic impedance signal to derive some measure of cardiac function, such as a measure of intra-ventricular or inter-ventricular mechanical dyssynchrony, and adaptively adjusts one or more pacing timing parameters so as to improve cardiac function. In one particular implementation, the device analyzes the cardiogenic impedance signal to derive a fractionation index representative of the degree of fractionation of the cardiogenic impedance signal. Pacing parameters are adaptively adjusted so as to decrease the degree of fractionation. The fractionation index may be derived, e.g., by simply counting a number of "notches" or "troughs" appearing within those portions of the impedance signal that are representative of individual heartbeats. The notches often correspond to periods of time when chambers of the heart are not beating uniformly, i.e. the greater the number of notches, the greater the degree of mechanical dyssynchrony. Alternatively, the fractionation index may be derived by determining the frequencies associated with the cardiogenic impedance signal. The greater the number of notches and troughs within the cardiogenic impedance signal, the higher the frequencies of the signal, and the greater the mechanical dyssynchrony. In either case, adaptively adjusting pacing parameters so as to decrease the fractionation index also serves to improve mechanical synchrony within the heart. Thus, a computationally simple procedure for optimizing pacing parameters to improve mechanical synchrony is provided, which does not require the device to directly evaluate cardiac output or stroke volume or other cardiac performance parameters adversely affected by mechanical dyssynchrony. Preferably, adjustments to the pacing parameters are made substantially in real-time. Lossy or lossless data compression techniques may be employed to minimize the amount of actual cardiogenic impedance data that needs to be stored and processed at any given time. Trends in cardiac function within the patient may also be identified and tracked to detect, for example, progression of CHF as evidenced by an increasing fractionation of the cardiogenic impedance signal. Appropriate warnings may be generated for the patient, the physician, or both.

The adaptive adjustment of pacing therapy using cardiogenic impedance signals may be performed in conjunction with one or more intracardiac electrogram (IEGM) signals. For example, a measure of electrical dyssynchrony may be derived from the IEGM signals while a measure of mechanical dyssynchrony is derived from the cardiogenic impedance signals, permitting both to be used in adjusting the pacing parameters. Still further, if the implanted device is equipped with a sensor to directly measure cardiac pressure (e.g., left atrial pressure (LAP) or LV end diastolic ($LV_{END}$) pressure), such pressure measurements may be used in conjunction with the cardiogenic impedance signals to adjust pacing parameters so as to reduce cardiac pressure while also reducing mechanical dyssynchrony. In some implementations, the pacing parameters are adaptively adjusted only when the patient is in a certain predetermined states as determined by activity sensor, posture detectors, etc. In one particular example, adaptive adjustment is only performed if the patient is at rest and in a supine posture. Adaptive adjustment may be still further limited to times when the blood oxygen saturation ($SO_2$) level of the patient is within a certain acceptable range. In implementations where multiple cardiogenic impedance signals are sensed along different sensing vectors, the implanted system may be equipped, e.g., with multiple electrodes per lead or with multiple leads per chamber. When using multiple electrodes on a given lead, it may be desirable to employ a helical lead configuration wherein proximal portions of the lead have a greater diameter than distal portions, so as to more readily accommodate the multiple electrodes.

BRIEF DESCRIPTION OF THE DRAWINGS

Further features and advantages of the invention may be more readily understood by reference to the following description taken in conjunction with the accompanying drawings, in which.

DESCRIPTION OF THE PREFERRED EMBODIMENTS

The following description includes the best mode presently contemplated for practicing the invention. The description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Overview of Implantable Medical System

Figure 1:
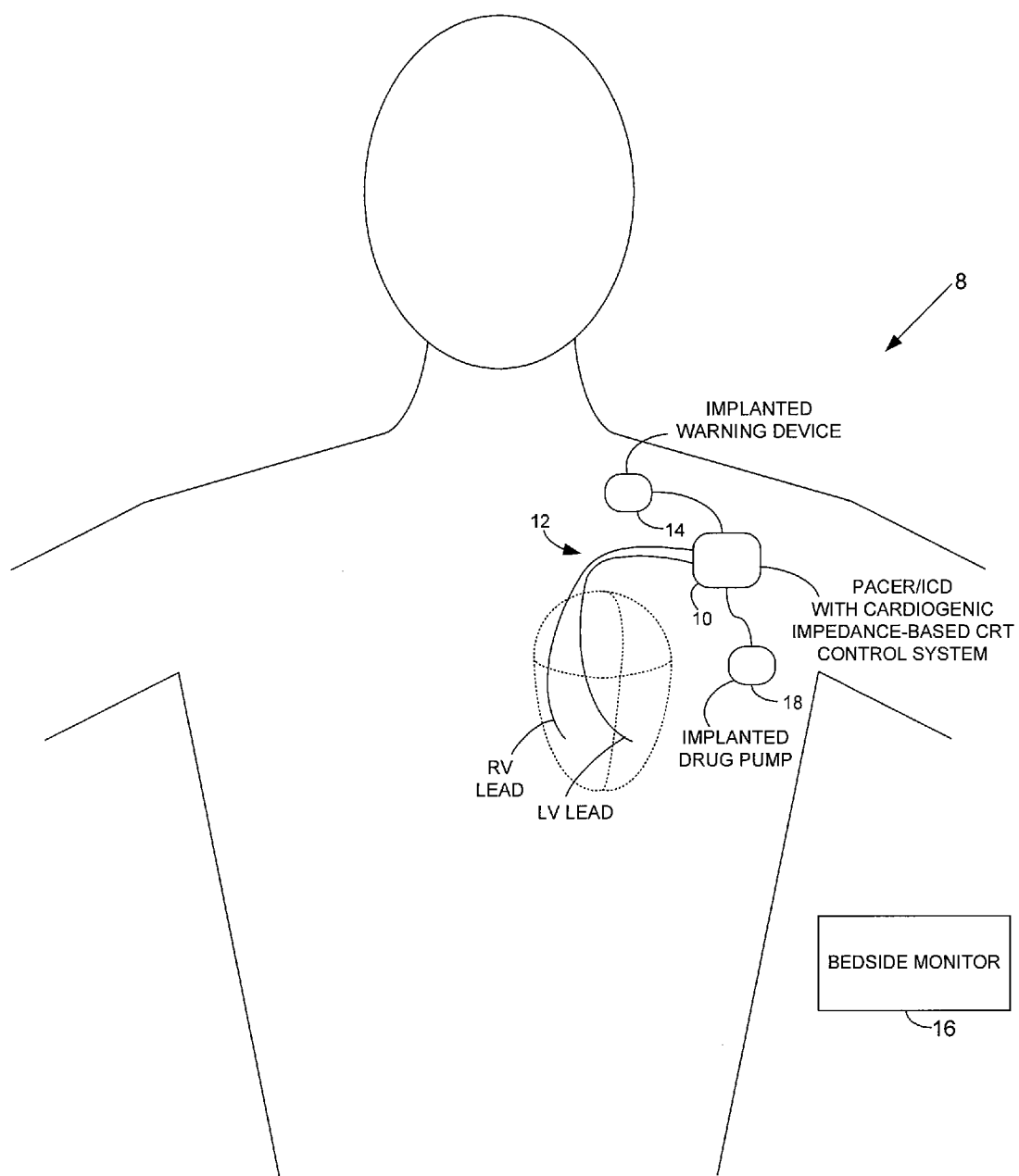
FIG. 1 is a stylized representation of an exemplary implantable medical system equipped with cardiogenic impedance-based adaptive CRT control.
Figure 12:
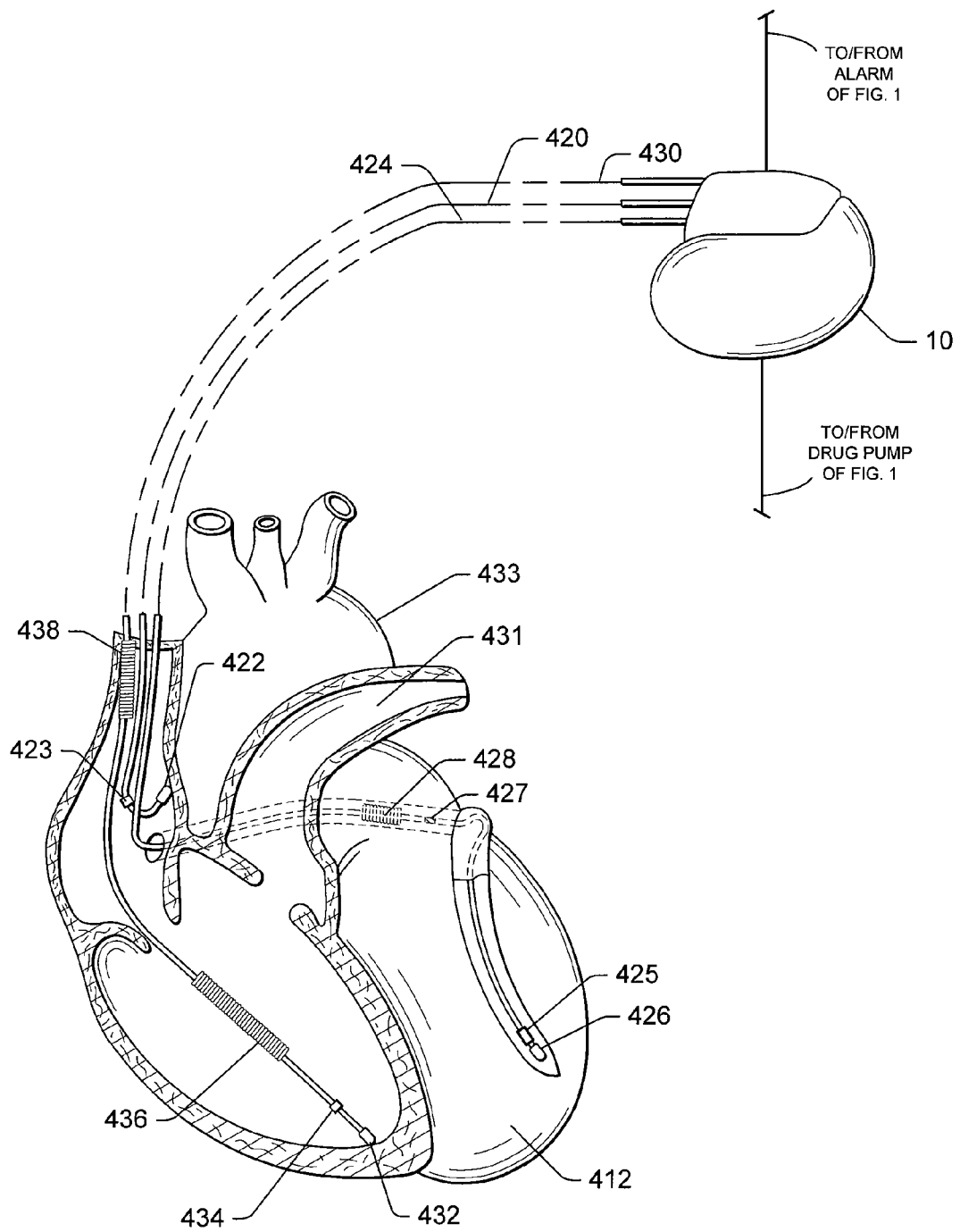
FIG. 12 is a simplified, partly cutaway view, illustrating the pacer/ICD of FIG. 1 along with at full set of leads implanted in the heart of the patient, which may be employed to perform cardiogenic impedance-based adaptive CRT control.

FIG. 1 provides a stylized representation of an exemplary implantable synaptic pacing medical system 8 capable of detecting cardiogenic impedance signals and adaptively adjusting therapy in response thereto, particularly CRT. To this end, implantable system 8 includes a pacer/ICD 10 or other cardiac stimulation device that incorporates internal components (shown individually in FIG. 13) for detecting one or more cardiogenic impedance signals using electrodes mounted to a set of sensing/pacing leads 12 and for adaptively adjusting pacing therapy delivered using those leads based on the cardiogenic impedance signals and other signals. In FIG. 1, only two leads are shown. A more complete set of leads is illustrated in FIG. 12, which is discussed below. Within the exemplary implementations described herein, pacing therapy is adjusted by adaptively adjusting pacing timing parameters, such as the AV delay and the LV-RV delay, so as to improve some measure of cardiac function derived from the cardiogenic impedance signals. For dual-chamber devices, the AV delay specifies the time delay between a paced or sensed atrial event and a paced ventricular event. For biventricular pacing devices, the LV-RV delay (sometimes also referred to as just the V-V delay) specifies the time delay between a paced or sensed right ventricular (RV) event and a paced left ventricular (LV) event. (This delay may be negative.) The measure of cardiac function may be, e.g., a measure of mechanical dyssynchrony between the left and right ventricles (i.e. an interventricular mechanical dyssynchrony) or a measure of mechanical dyssynchrony occurring within a particular heart chamber (i.e. an intra-ventricular mechanical dyssynchrony or an intra-atrial mechanical dyssynchrony.) As will be explained, other measures of cardiac function may additionally or alternatively be employed, such as measures based on LAP or $LV_{END}$ pressure or other factors. Preferably, the adaptive adjustments are performed substantially in real-time so as to maintain the pacing timing parameters at or near optimal values at all times.

In this regard, normal, healthy hearts display a monotonically increasing relation between $LV_{END}$ pressure and cardiac output. However, in heart failure patients, this relation is compromised. That is, the cardiac output curve varies little over a wide range of pressure values. Consequently, the pacer/ICD is programmed to control cardiac pressure, rather than cardiac output, by appropriately adjusting biventricular pacing therapy, such as CRT. With CRT, the pacer/ICD paces both ventricles of the heart based on predetermined timing sequences. Typically, the right atrium is paced first. Then, after a set AV delay, the device paces the left ventricle. To allow for the delayed LV contraction caused by heart failure, the RV is usually paced last, after a set LV-RV delay. The pacer/ICD adjusts either one or both of the AV and LV-RV delays such that LAP or $LV_{END}$ pressure are brought into normal ranges. One premise underlying this approach is based on the knowledge that lower pressures promote heart remodeling that, in time, tend to reduce the enlargement of ventricles and atria. As the heart dimension trends back to normal values, the strength of the cardiac muscle increases, resulting in increased cardiac output. Rather than using pressure as the direct control feedback parameter, the pacer/ICD uses cardiogenic impedance to regulate therapy with the goal of reducing blood pressure levels. As an illustrative example, the cardiogenic impedance recorded between electrodes in the LV and RA is used to estimate changes in LAP. As the impedance morphology becomes more fractioned and notches and troughs therein become more frequent, that indicates an increased level of LAP or $LV_{END}$ pressure. (Fractionation of the cardiogenic impedance signal is described more fully below, along with the notches and troughs appearing herein.) Conversely, as the LV-RA cardiogenic impedance resolves back from the fractionated morphology to normal morphology, that indicates that LAP or $LV_{END}$ pressure decreases towards normal values. As will be explained, this can be achieved using any of a number of techniques. For example, the peaks or troughs seen in the impedance morphology can be counted by a counter inside pacer/ICD. When the frequency of their occurrence is high, the AV or LV-RV timing can be adjusted from a set value (determined, for example, at implant time) to lower or higher values, with the goal of decreasing the feature occurrence frequency. The timing adjustment can be first tried in one direction, for example from original AV or LV-RV timing delays to higher values. If this adjustment results in a decreased frequency of occurrence for the peaks and troughs, then the adjustment is continued in this direction until the LV-RA impedance waveform trends close to normal morphologies. Otherwise, the direction of the timing delay adjustment is reversed and values are decremented from initial settings to lower numbers. Alternatively, other impedance characteristics, or other vectors from a multi-vector network, that correlate with LAP and $LV_{END}$ pressure, such as peak-to-peak amplitudes, can be used to adjust the A-V and LV-RV timing.

Additionally, the pacer/ICD can track trends in cardiac function, such as a trend toward increasing mechanical dyssynchrony, and issues warning signals, if warranted. For example, if mechanical dyssynchrony exceeds an acceptable threshold, warning signals are generated to warn the patient, using either an internal warning device 14 or an external bedside monitor 16. Internal warning device 14 may be a vibrating device or a "tickle" voltage device that, in either case, provides perceptible stimulation to the patient to alert the patient so that the patient may consult a physician. In one example, once the tickle warning is felt, the patient positions an external warning device above his or her chest. The handheld device receives short-range telemetry signals from the implanted device and provides audible or visual verification of the warning signal. The handheld warning device thereby provides confirmation of the warning to the patient, who may be otherwise uncertain as to the reason for the internally generated warning signal. For further information regarding this warning/notification technique, see U.S. patent application Ser. No. 11/043,612, of Kil et al., filed Jan. 25, 2005, entitled "System and Method for Distinguishing Among Ischemia, Hypoglycemia and Hyperglycemia Using an Implantable Medical Device."

If a bedside monitor is provided, the bedside monitor provides audible or visual alarm signals to alert the patient as well as textual or graphic displays. In addition, diagnostic information pertaining to the deteriorating cardiac condition is transferred to the bedside monitor or is stored within the pacer/ICD for subsequent transmission to an external programmer (not shown in FIG. 1) for review by a physician or other medial professional. The physician may then prescribe any other appropriate therapies to address the condition. The physician may also adjust the operation of the pacer/ICD to activate, deactivate or otherwise control any therapies that are automatically applied. The bedside monitor may be directly networked with a centralized computing system, such as the HouseCall™ system of St. Jude Medical, for immediately notifying the physician of any significant deterioration in cardiac function. Networking techniques for use with implantable medical systems are set forth, for example, in U.S. Pat. No. 6,249,705 to Snell, entitled "Distributed Network System for Use with Implantable Medical Devices".

In addition to the adaptive adjustment of the pacing parameters, other forms of therapy may also be controlled by the pacer/ICD in response to changes in the cardiac function. In this regard, if the implanted system is equipped with a drug pump, appropriate medications may be automatically administered upon detection of a significant deterioration in cardiac function. For example, heart failure medications may be delivered directly to the patient via the drug pump, if warranted. Exemplary heart failure medications include ACE inhibitors, diuretics, digitalis and compounds such as capto-pril, enalapril, lisinopril and quinapril. Depending upon the particular medication, alternative compounds may be required for use in connection with an implantable drug pump. Routine experimentation may be employed to identify medications for treatment of heart failure or other conditions that are safe and effective for use in connection with an implantable drug pump. Dosages may be titrated based upon the severity of heart failure. Various techniques may be employed to confirm the detection of heart failure (or other medical conditions) made by the device based on the analysis of the cardiogenic impedance signals before drug therapy is delivered. Exemplary heart failure detection/evaluation techniques are set forth in: U.S. Pat. No. 6,748,261, entitled "Implantable Cardiac Stimulation Device for and Method of Monitoring Progression or Regression of Heart Disease by Monitoring Interchamber Conduction Delays"; U.S. Pat. No. 6,741,885, entitled "Implantable Cardiac Device for Managing the Progression of Heart Disease and Method"; U.S. Pat. No. 6,643,548, entitled "Implantable Cardiac Stimulation Device for Monitoring Heart Sounds to Detect Progression and Regression of Heart Disease and Method Thereof"; U.S. Pat. No. 6,572,557, entitled "System and Method for Monitoring Progression of Cardiac Disease State using Physiologic Sensors"; and U.S. Pat. No. 6,480,733, entitled "Method for Monitoring Heart Failure", each assigned to Pacesetter, Inc.

Hence, FIG. 1 provides an overview of an implantable system capable of adaptively controlling pacing therapy based on cardiogenic impedance signals, for delivering any appropriate warning/notification signals, and for delivering medications, when warranted. Embodiments may be implemented that do not necessarily perform all of these functions. For example, embodiments may be implemented that provide only for adaptive adjustment of pacing therapy but not for delivering warning signals. Moreover, systems provided in accordance with the invention need not include all of the components shown in FIG. 1. In many cases, for example, the system will include only a pacer/ICD and its leads. Implantable warning devices and drug pumps are not necessarily implanted. Some implementations may employ an external monitor for displaying warning signals without any internal warning device. These are just a few exemplary embodiments. No attempt is made herein to describe all possible combinations of components that may be provided in accordance with the general principles of the invention. In addition, note that the particular locations of the implanted components shown in FIG. 1 are merely illustrative and may not necessarily correspond to actual implant locations. Although internal signal transmission lines provided are illustrated in FIG. 1 for interconnecting the various implanted components, wireless signal transmission may alternatively be employed.

Overview of Adaptive Therapy Control Using Cardiogenic Impedance

Figure 2:
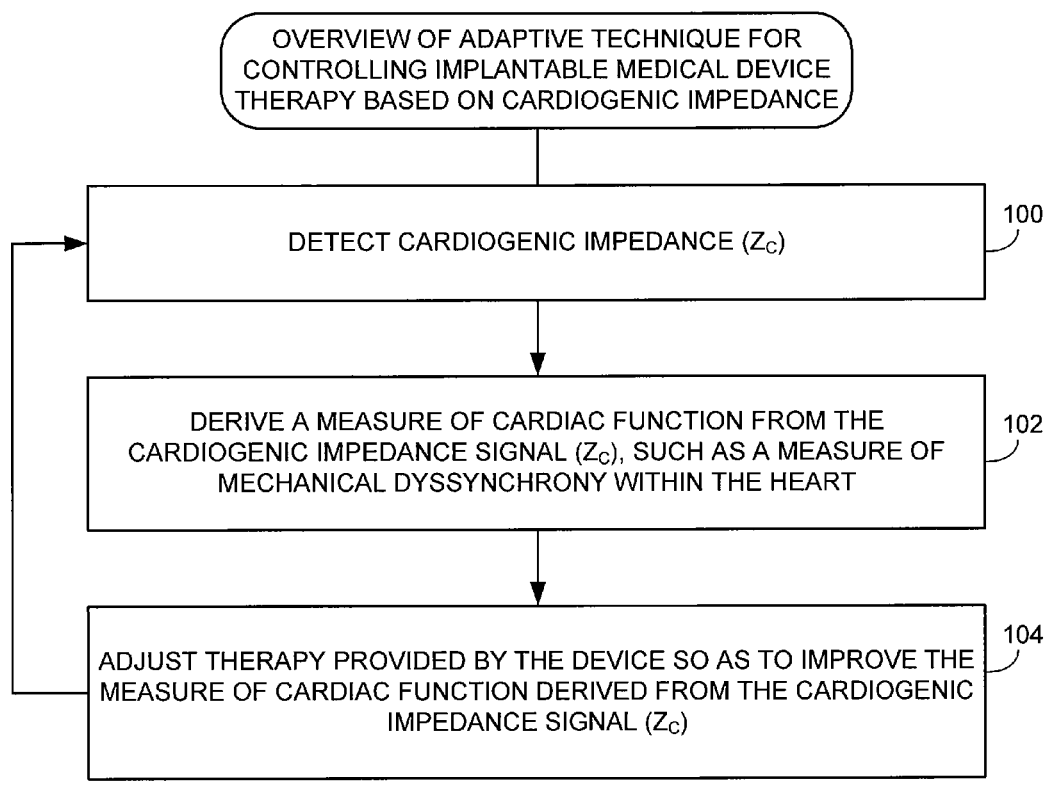
FIG. 2 is a flow diagram providing an overview of cardiogenic impedance-based adaptive therapy control techniques that may be performed by the system of FIG. 1.

FIG. 2 provides an overview of cardiogenic impedance-based therapy control techniques that may be performed by the pacer/ICD of FIG. 1 or other implantable device. At step 100, the pacer/ICD detects cardiogenic impedance ($Z_C$). A cardiogenic impedance signal is an impedance signal representative of the beating of the heart of the patient in which the device is implanted. The cardiogenic impedance signal is sensed along a sensing vector passing through at least a portion of the heart so that the sensed impedance is affected by the mechanical beating of the heart along that sensing vector. For example, the cardiogenic impedance signal may be sensed between an LV tip electrode and an RV tip electrode or between the RV tip electrode and an RA tip electrode, where RA refers to the right atrium. Depending up on the particular sensing vector, it may be appropriate to filter the cardiogenic impedance signal to eliminate or reduce any non-cardiogenic components such as any components arising due to respiration or changes in body position of posture. Bandpass filtering is typically sufficient to filter out respiratory components. Multiple cardiogenic impedance signals may be sensed using different sensing vectors passing through different portions of the heart so as to be representative of the beating of different chambers of the heart or different portions of the myocardium. To this end, the implanted system may be equipped, e.g., with multiple electrodes per lead or with multiple leads per chamber. Unipolar or bipolar sensing systems may be employed.

Preferably, a tri-phasic impedance pulse waveform is employed to sense the cardiogenic impedance signal. The tri-phasic waveform is a frequency-rich, low energy waveform that provides a net-zero charge and a net-zero voltage. An exemplary tri-phasic pulse waveform is described in detail in the related patent applications, cited above. For convenience, a portion of that description will now be provided herein. The tri-phasic waveform possesses many special waveform features and electrical characteristics that are well suited for probing and measuring many types of physiological parameters in the body using current modulated or voltage modulated pulses. The waveform has negative phases (pulse segments below baseline) that balance positive phases (pulse segments above baseline). Other versions of the waveform may have more than three phases, may be synchronous or asynchronous, may be rectangular or sinusoidal, etc. One version of the waveform uses the sinc(x) sampling waveform. Typically, the tri-phasic waveform is applied as a current waveform with the resulting voltage being sensed. Alternatively, the waveform is applied as a voltage waveform and sensed as electrical current. In the following descriptions, a current waveform is assumed, unless otherwise noted.

Advantageous properties of the waveform include superior penetration of some tissues than conventionally injected signals; better differential penetration of tissues than conventionally injected signals for improved differentiation and characterization of tissues; broader frequency spectrum content than conventionally injected signals in order to characterize tissue; greater neutrality in the body than conventionally injected signals, i.e., the exemplary waveforms do not change the parameter they are trying to measure, and moreover, do not create ionic imbalances or imbalances of charge, voltage, etc., in the tissues or at tissue-electrode interfaces. The waveform preferably has a total duration less than the charging time constant of the electrode-electrolyte interfaces used to inject and sense the signals. These time constants are typically in the range of a few milliseconds. In one implementation, the duration of the waveform is less than 1 millisecond. This waveform feature is helpful for minimizing polarization effects at these electrode-electrolyte interfaces. Other features of the waveform include symmetric or asymmetric phase duration, decreasing phase amplitudes, and alternating phase signs. The waveform preferably has null durations in between phases to provide time to allow complete processing of information caused by one phase before the next phase of the waveform begins. Implementations of the waveform that have near perfect square wave pulses (or rectangular wave pulses) contain a great deal of high-frequency content. Near-sinusoidal implementations of the waveform may contain less high frequency content than the rectangular wave versions.

The features of exemplary waveforms just enumerated provide numerous advantages, including: eliminating the need for fast digital sampling, minimizing artifacts introduced in the measurement process, increased tolerance of small phase delays between injected and sensed signals. The waveform also lends itself to CMOS realization using low-value switched capacitor solutions. Further, the wide frequency spectrum of the injected signal can be used to implement algorithms that differentiate tissues based on their frequency response, and/or phase delay. The very low duty-cycle of the waveform makes them safer for patients. The reduced duty-cycle brings the injected charge and the root-mean-square value of the injected signal well below levels that could be perceived by the patient or that could induce adverse events.

It is important to note that the net-zero voltage feature, also referred to as the voltage-balanced feature, refers to the voltage formed on blocking capacitors that appear in series with the load. The flow of current through these capacitors builds up voltage across them. Since these capacitors also appear in circuits that are responsible for sensing cardiac activity, it is important that the net voltage built up on them be zero. As a result of the net-zero voltage feature, the influence of the waveform on the circuits that sense cardiac activity is minimal. Other features of the waveform derive from the above-mentioned null segments—intra-waveform segments containing no signal—that serve several purposes. First, the null segments allow the electronics in processing circuits to settle during measurement of phases and second, they allow multiple instances of the waveform to exist in the patient's tissue simultaneously, being staggered by time multiplexing such that a phase of one waveform can be measured during the time that there is no signal between phases of another waveform.

In the preferred implementation, the waveform is used to derive physiological measurements based on intracardiac impedances, i.e. cardiogenic impedance measurements. Based on such cardiogenic impedance measurements, many physiological variables can be trended to detect changes in a patient's condition, such as changes in CHF, pulmonary edema, systolic slope, contraction (e.g., $dZ_C/dt(max)$), diastolic slope, relaxation (e.g., $dZ_C/dt(min)$), pre-ejection period (in low resolution), ejection time, left ventricular ejection fraction (LVEF), diastolic heart failure index (DHFI), cardiac index, etc.

The waveform provides an elegant and reliable vehicle for measuring bodily impedances in a manner that gives reliably reproducible results. Instead of a conventional technique of trying to sense an instantaneous "snapshot" measurement of a conventionally injected signal, the circuitry of the pacer/ICD derives an impedance measurement by dividing the area under the sensed voltage curve by the area of the injected current waveform. The pacer/ICD can perform this exemplary method by "integrating the curve" of an absolute value of the waveforms. Sometimes the exemplary implantable device can closely approximate this integration without having to perform an integration operation by directly measuring and summing the area "under" the curve (e.g., under the rectangular wave) of the sensed voltage waveform, that is, the area composed of the absolute value of the three areas of the three phases of an exemplary tri-phasic current waveform.

Likewise, the pacer/ICD can integrate, or closely approximate the integration, by measuring and summing the area "under" the curve (e.g., the rectangular wave) of the sensed voltage waveform, that is, the area composed of the absolute value of the three areas of the three phases. In one implementation, the area of the sensed voltage waveform is measured at the output of an integrator circuit. The area of the injected current waveform is computed by, or preset by, the microcontroller driving the implantable device. The pacer/ICD may thus use this area-based ("areal") approach to deriving a network of impedance measurements over a multi-vector network.

At step 102, the pacer/ICD derives a measure of cardiac function from the cardiogenic impedance signal ($Z_C$), such as a measure of mechanical dyssynchrony within the heart. In one particular example to be described below, the measure of cardiac function is a fractionation index representative of a degree of fractionation of the cardiogenic impedance signal, which is, in turn, representative of mechanical dyssynchrony within the heart. However, other measures of cardiac function may be derived from the cardiogenic impedance signal, such as LAP, $LV_{END}$ pressure, or other parameters. Moreover, the measure of cardiac function derived from cardiogenic impedance may be supplemented, in some implementations, by measures of cardiac function derived from other sources, such as from an IEGM or from direct measurements of cardiac pressure obtained from a pressure sensor, if provided, or from direct measurements of cardiac performance, such as direct measurements of stroke volume or cardiac output.

At step 104, the pacer/ICD then adjusts therapy so as to improve the measure of cardiac function derived from the cardiogenic impedance signal $Z_C$. Steps 100-104 are repeated in a closed loop so as to adaptively adjust the therapy. Preferably, the adjustments are made substantially in real-time so as to continuously, or at least very frequently, adjust therapy in response to changes in cardiac function as derived from the cardiogenic impedance signal or from other sources. This allows the pacer/ICD to respond promptly to changes within the heart of the patient. To achieve real-time or near real-time performance, the pacer/ICD preferably adjusts therapy based only on computationally simple measurements derived from the cardiogenic impedance signals, such as the aforementioned fractionation index. As such, supplemental measures of cardiac function, such as LAP, stroke volume etc., are not necessarily explicitly calculated. Moreover, lossy data compression may be performed to reduce the amount of cardiogenic impedance data to be stored and processed at any given time. This is particularly advantageous if multiple cardiogenic impedance signals are measured along different sensing vectors or if data is to be stored over a long term for trending purposes.

Figure 3:
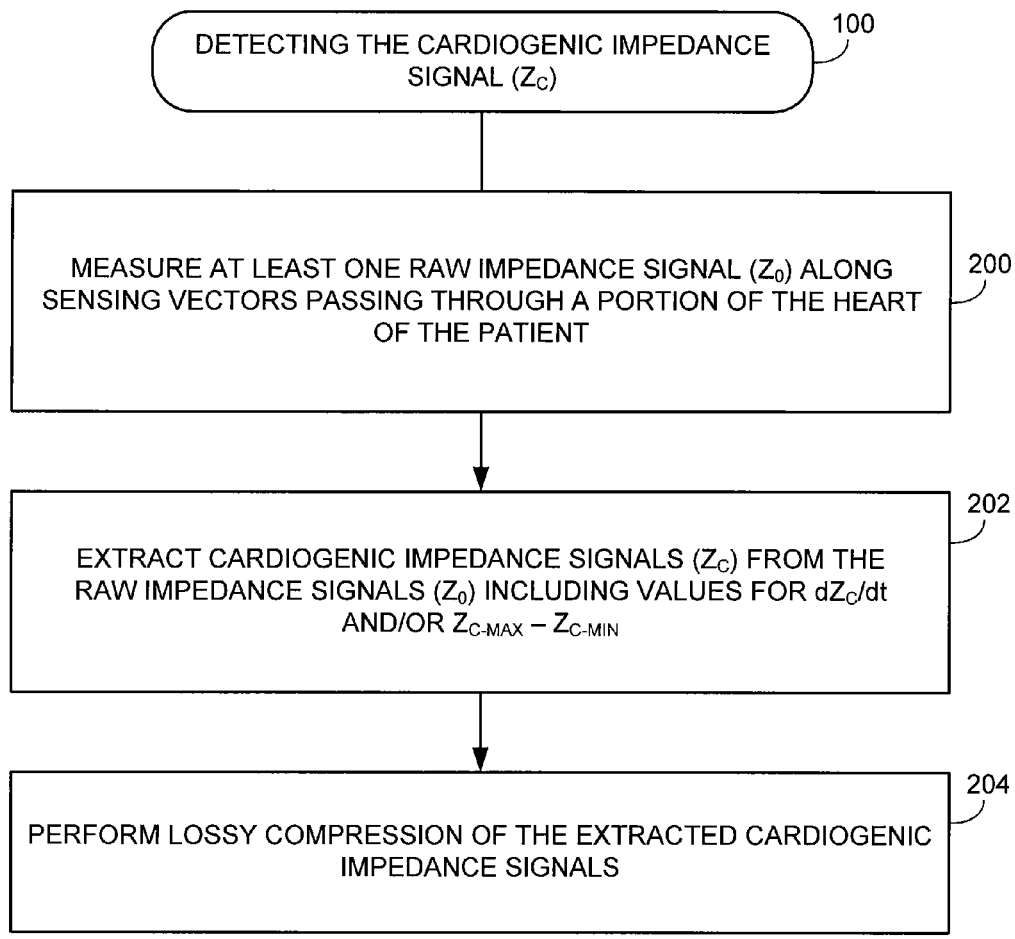
FIG. 3 is a flow diagram illustrating exemplary techniques for detecting cardiogenic impedance in accordance with the general technique of FIG. 2.

FIG. 3 illustrates an exemplary technique for detecting cardiogenic impedance for use at step 100 of FIG. 2. Beginning at step 200, the pacer/ICD measures at least one raw impedance signal ($Z_0$) along at least one sensing vector passing through a portion of the heart of the patient. The raw impedance signal includes cardiac components (i.e. variations arising due to the beating of the patient's heart) and, depending upon the particular sensing vector used, may also include respiratory components and/or components arising due to patient activity or changes in posture or position. At step 202, the pacer/ICD extracts cardiogenic impedance signals ($Z_C$) from the raw impedance signals ($Z_0$) including values representative of the rate of change of $Z_C$ with time (i.e. $dZ_C/dt$) and/or values representative of the peak-to-peak magnitude of $Z_C$ (i.e. $Z_{C-MAX}$-$Z_{C-MIN}$). As noted, the cardiogenic components can typically be extracted using filtering techniques. Exemplary filtering techniques are discussed in the related applications, cited above. At step 204, if needed, the pacer/ICD performs lossy compression of the extracted cardiogenic impedance signals. That is, the pacer/ICD reduces the amount of cardiogenic impedance data to be stored at any given time by selectively storing only a portion of the data. This is particularly appropriate for real-time processing. Otherwise conventional lossy compression techniques may be employed. Typically, the more uniform the data, the more the data can be compressed without loss.

Figure 4:
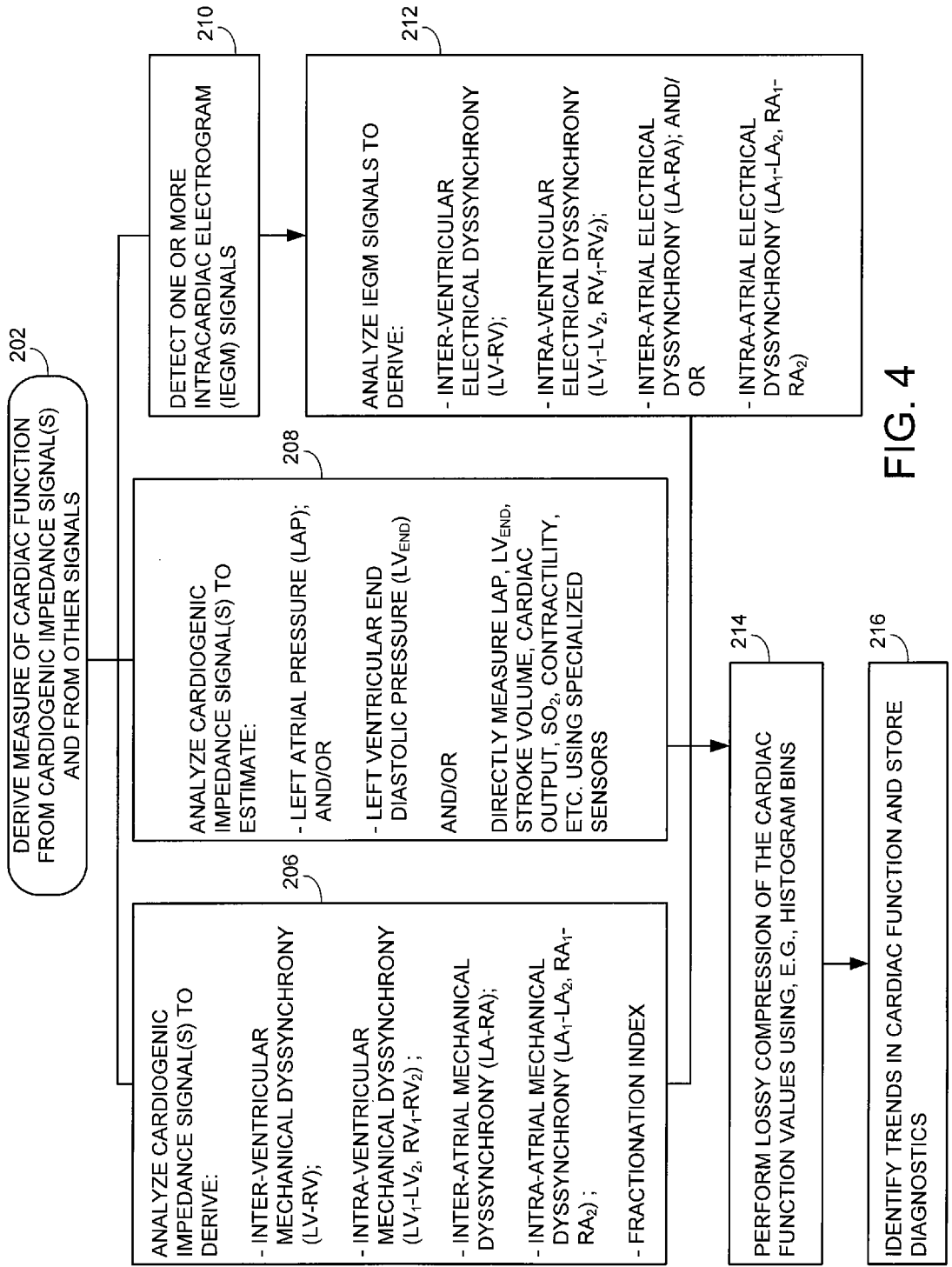
FIG. 4 is a flow diagram illustrating exemplary techniques for deriving a measure of cardiac function in accordance with the general technique of FIG. 2.

FIG. 4 illustrates various techniques for deriving a measure of cardiac function from the cardiogenic impedance signals and from other signals, as well, for use at step 102 of FIG. 2. Although multiple techniques are illustrated, the pacer/ICD need not implement each of the techniques. The list in not exhaustive. Indeed, as already noted, it is typically sufficient to merely derive a fractionation index from the cardiogenic impedance signals. Multiple techniques are illustrated, in part, for the sake of completeness. Beginning at step 206, the pacer/ICD analyzes cardiogenic impedance signal(s) to derive one or more of: inter-ventricular mechanical dyssynchrony (LV-RV); intra-ventricular mechanical dyssynchrony ($LV_1$-$LV_2$, $RV_1$-$RV_2$); inter-atrial mechanical dyssynchrony (LA-RA); intra-atrial mechanical dyssynchrony ($LA_1$-$LA_2$, $RA_1$-$RA_2$); and a fractionation index. Inter-ventricular mechanical dyssynchrony pertains to any dyssynchrony between the mechanical contractions of the left and right ventricles and may be detected by the pacer/ICD be evaluating a time delay, if any, between corresponding notches within LV and RV cardiogenic impedance signal associated with those contractions, such as between an LV unipolar cardiogenic impedance signal and an RV unipolar cardiogenic impedance signal. Similar considerations apply to inter-atrial mechanical dyssynchrony. Intra-ventricular mechanical dyssynchrony instead pertains to any dyssynchrony between the contractions of a first portion of one ventricle and a second portion of the same ventricle and may be detected by the pacer/ICD be evaluating a time delay, if any, between corresponding notches within separate cardiogenic impedance signal associated with those two portions, such as between a first unipolar cardiogenic impedance signal ($Z_{LV1}$) sensed using an electrode positioned near the apex of the LV and a second unipolar cardiogenic impedance signal sensed using an electrode positioned at the opposing end of the LV ($Z_{LV2}$). Similar considerations apply to intra-atrial mechanical dyssynchrony. As can be appreciated, multiple mechanical dyssynchrony values can be obtained along different sensing vectors depending upon the number and location of electrodes used.

Insofar as the fractionation index is concerned, the index is representative of a degree of fractionation of the cardiogenic impedance signal. The fractionation index may be derived, e.g., by simply counting a number of notches appearing within portions of the signal representative of individual heartbeats. A patient whose heartbeat exhibits five notches has a higher degree of fractionation than a patient whose heartbeat exhibits only four notches. As noted, the notches often correspond to periods of time when chambers of the heart are not beating uniformly, i.e. the greater the number of notches, the greater the degree of mechanical dyssynchrony. Though, even a healthy and fully synchronized heart will exhibit some notches within the cardiogenic impedance signals. That is, for a normal patient free of heart failure, the characteristic morphology of a cardiogenic impedance pattern for a single heartbeat shows relatively smooth waves that follow the cardiac cycle, with relatively little raggedness (i.e., "fractionation") at the crest of each impedance peak (or trough). During early onset of heart failure, the cardiogenic impedance pattern for a single heartbeat develops a characteristic morphology of notches in or near the crests—i.e., a moderate degree of fractionation. During late heart failure conditions, cardiogenic impedance pattern for a single heartbeat develops a characteristic morphology of high volatility and fractionation, where the magnitude of the notches increases significantly and their frequency of occurrence is high. The fractionation index may also be derived by determining the frequencies associated with the cardiogenic impedance signal using, for example, a Fast Fourier Transform (FFT). The greater the number of notches and troughs within the cardiogenic impedance signal, the higher the frequencies of the signal, and the greater the mechanical dyssynchrony. Techniques for identifying and comparing notches and troughs within a cardiogenic impedance signal are discussed in the related patents, cited above.

At step 208, the pacer/ICD also analyzes the cardiogenic impedance signal(s) to estimate LAP and/or $LV_{END}$. Techniques for evaluating cardiac pressure using a cardiogenic impedance signal are also discussed in the related patents, cited above. Additionally or alternatively, the pacer/ICD directly measures LAP, $LV_{END}$ pressure, stroke volume, cardiac output, $SO_2$, contractility, or any other physiological parameter representative of some aspect of cardiac function using one more specialized sensors. Techniques for detecting blood oxygen saturation using an implantable medical device are described in: U.S. patent application Ser. No. 11/378,604, of Kroll et al., filed Mar. 16, 2006, entitled, "System and Method for Detecting Arterial Blood Pressure based on Aortic Electrical Resistance using an Implantable Medical Device," now U.S. Pat. No. 7,654,964. Techniques for detecting blood pressure are described in: U.S. Pat. No. 5,615,684 to Hagel, et al., entitled "Medical Device for Detecting Hemodynamic Conditions of a Heart" and U.S. Pat. No. 6,575,912 to Turnoff, entitled "Assessing Heart Failure Status Using Morphology of a Signal Representative of Arterial Pulse Pressure." Techniques for detecting contractility are described in: U.S. Pat. No. 5,800,467 to Park et al., entitled "Cardio-Synchronous Impedance Measurement System for an Implantable Stimulation Device", Techniques for detecting stroke volume and/or cardiac output are described in U.S. patent application Ser. No. 11/267,665, filed Nov. 4, 2005, of Kil et al., entitled "System and Method for Measuring Cardiac Output via Thermal Dilution using an Implantable Medical Device with Thermistor Implanted in Right Ventricle," now abandoned.

At step 210, the pacer/ICD also detects one or more IEGM signals, preferably including LV and RV IEGM signals. At step 212, the pacer/ICD analyzes the IEGM signals to derive one or more of: inter-ventricular electrical dyssynchrony (LV-RV); inter-atrial electrical dyssynchrony (LA-RA); intra-ventricular electrical dyssynchrony ($LV_1$-$LV_2$, $RV_1$-$RV_2$) and/or intra-atrial electrical dyssynchrony ($LA_1$-$LA_2$, $RA_1$-$RA_2$). Inter-ventricular electrical dyssynchrony pertains to any dyssynchrony between the electrical depolarization of the left and right ventricles and may be detected by the pacer/ICD be evaluating a time delay, if any, between corresponding features within LV and RV IEGM signals associated with depolarization, such as between an R-wave within the LV IEGM and the same R-wave within an RV IEGM. Similar considerations apply to inter-atrial electrical dyssynchrony. Intra-ventricular electrical dyssynchrony instead pertains to any dyssynchrony between the electrical depolarization of a first portion of the myocardium of one ventricle and a second portion of the myocardium of the same ventricle and may be detected by the pacer/ICD by evaluating a time delay, if any, between corresponding electrical features within separate IEGM signals associated with those two portions, such as between a first unipolar LV IEGM (i.e. LV-$IEGM_1$) sensed using an electrode positioned near the apex of the LV and a second unipolar IEGM signals sensed using an electrode positioned at the opposing end of the LV (i.e. LV-$IEGM_2$). Similar considerations apply to intra-atrial electrical dyssynchrony. As can be appreciated, multiple electrical dyssynchrony values can be obtained along different sensing vectors depending upon the number and location of electrodes used.

At step 214, the pacer/ICD records the various measures and/or parameters representative of cardiac function detected within steps 206-212. In many cases, multiple parameters may be combined to provide a combined measure or "metric" of cardiac function. Efficient techniques for combining different parameters into a single metric value for evaluation are set forth in U.S. patent application Ser. No. 10/339,989 to Koh et al., entitled "System and Method for Detecting Circadian States Using an Implantable Medical Device", filed Jan. 10, 2003. Again, lossy compression techniques are preferably used, when appropriate, to reduce the amount of data to be stored. In one example, histograms are used to store a compressed representation of the data. For example, if the fractionation index is determined by counting the number of notches within the cardiogenic signal associated with each individual heartbeat, a corresponding histogram bin may then be incremented. That is, whenever four notches are detected within a single heartbeat, a corresponding bin is incremented. Whenever five notches are instead detected within a single heartbeat, a different corresponding bin is incremented; and so on. Ultimately, the histogram will represent the distribution of fractionation of the cardiogenic impedance signal. Changes in the shape of the histogram over time are thereby representative of a trend toward increasing or decreasing fractionation. Trends in fractionation, or in any of the other measures of cardiac function detected, are identified at step 216, and appropriate diagnostics are generated and stored.

Figure 5:
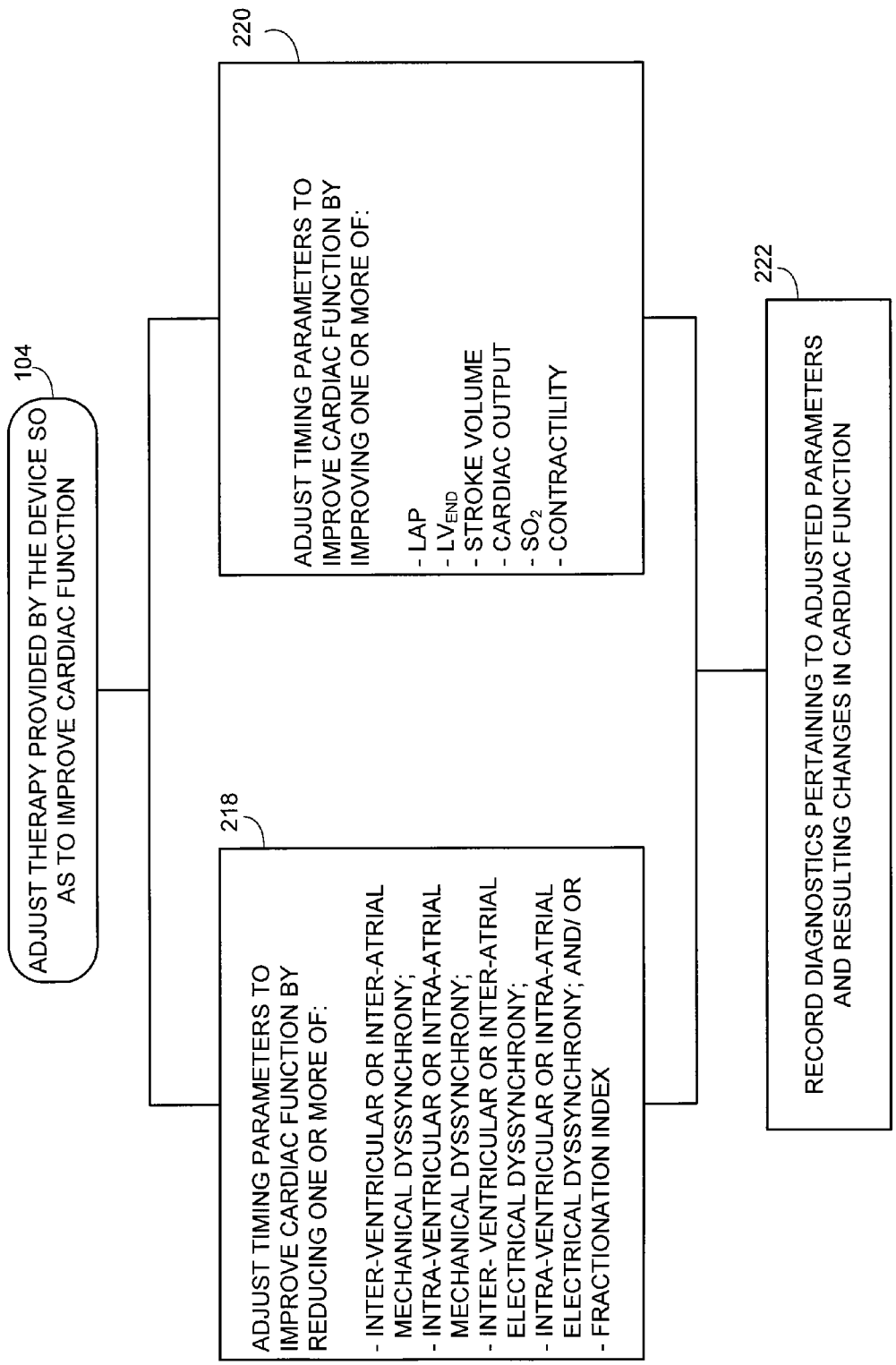
FIG. 5 is a flow diagram illustrating exemplary techniques for adaptively adjusting therapy based on the measure of cardiac function in accordance with the general technique of FIG. 2.

FIG. 5 illustrates various techniques for adjusting therapy so as to improve cardiac function for use at step 104 of FIG. 2. Although a number of techniques are illustrated, the pacer/ICD need not implement each of the techniques. The list in not exhaustive. At step 218, the pacer/ICD automatically and adaptively adjusts pacing timing parameters to reduce one or more of: inter-ventricular mechanical dyssynchrony (LV-RV); intra-ventricular mechanical dyssynchrony ($LV_1$-$LV_1$, $LV_1$-$LV_1$); inter-ventricular electrical dyssynchrony (LV-RV); intra-ventricular electrical dyssynchrony ($LV_1$-$LV_1$, $LV_1$-$LV_1$); inter-atrial mechanical dyssynchrony (LV-RV); intra-atrial mechanical dyssynchrony ($LV_1$-$LV_1$, $LV_1$-$LV_1$); inter-atrial electrical dyssynchrony (LV-RV); intra-atrial electrical dyssynchrony ($LV_1$-$LV_1$, $LV_1$-$LV_1$); and/or fractionation index. At step 220, the pacer/ICD additionally, or alternatively, adjusts timing parameters to improve cardiac function by improving one or more of: LAP, $LV_{END}$ pressure, stroke volume, cardiac output, $so_2$, contractility, etc. whether detected using specialized sensors or derived from the cardiogenic impedance signals. If multiple measures of cardiac function are employed, they are preferably combined into a single metric.

The specific timing parameters to be adjusted at steps 218 and 220 may depend upon the particular measure or metric value representative of cardiac function. Typically, at least, AV and LV-RV timing parameters are adjusted. Advantageously, the direction and magnitude of the adjustment need not be known in advance. Rather, the pacer/ICD makes an incremental adjustment in one timing parameter in one direction, then determines whether the adjustment improved the cardiac function of the patient or not. If an improvement is gained, the pacer/ICD makes an additional incremental adjustment in that timing parameter in that same direction in an attempt to achieve still further improvement. If the adjustment has an adverse effect, the pacer/ICD makes an incremental adjustment in the same timing parameter but in the opposite direction in an attempt to achieve an improvement in cardiac function. The magnitudes of the adjustments are adaptively varied so as to further optimize the parameter. If the initial adjustment had no effect, the pacer/ICD selects a different timing parameter to adjust. Once a particular parameter is optimized, the pacer/ICD can select a different parameter. For example, once AV delay has been optimized, LV-RV may then be optimized. The range within which the parameters are automatically adjusted can be restricted via device programming to ensure that the parameters remain within acceptable bounds.

Various additional techniques and strategies for adaptively optimizing pacing parameters may be employed, where appropriate, to supplement or enhance the techniques described herein. Examples are set forth in: U.S. patent application Ser. No. 11/231,081, filed Sep. 19, 2005, of Turcott, entitled "Rapid Optimization of Pacing Parameters"; U.S. patent application Ser. No. 11/199,619, filed Aug. 8, 2005, of Gill et al, entitled "AV Optimization Using Intracardiac Electrogram"; U.S. patent application Ser. No. 11/366,930, of Muller et al., filed Mar. 1, 2006, entitled "System and Method for Determining Atrioventricular Pacing Delay based on Atrial Repolarization"; U.S. patent application Ser. No. 10/928,586, of Bruhns et al., entitled "System and Method for Determining Optimal Atrioventricular Delay based on Intrinsic Conduction Delays", filed Aug. 27, 2004; and U.S. Pat. No. 6,522,923 to Turcott, entitled "Methods, Systems and Devices for Optimizing Cardiac Pacing Parameters Using Evolutionary Algorithms."

At step 222, diagnostic information pertaining to the adjusted parameters and to any resulting changes in cardiac function are stored for subsequent physician review via an external programmer device. Depending upon the programming of the pacer/ICD, the physician can then modify the adaptive procedures employed by the pacer/ICD, if warranted, so as to improve the efficacy of the procedures by, e.g., changing the range in which timing parameters are adaptively adjusted or by changing the order in which parameters are optimized.

Having provided an overview of the adaptive adjustment techniques of the invention, the following section will now illustrate some specific examples.

Exemplary Adaptive Therapy Control Implementations

Figure 6:
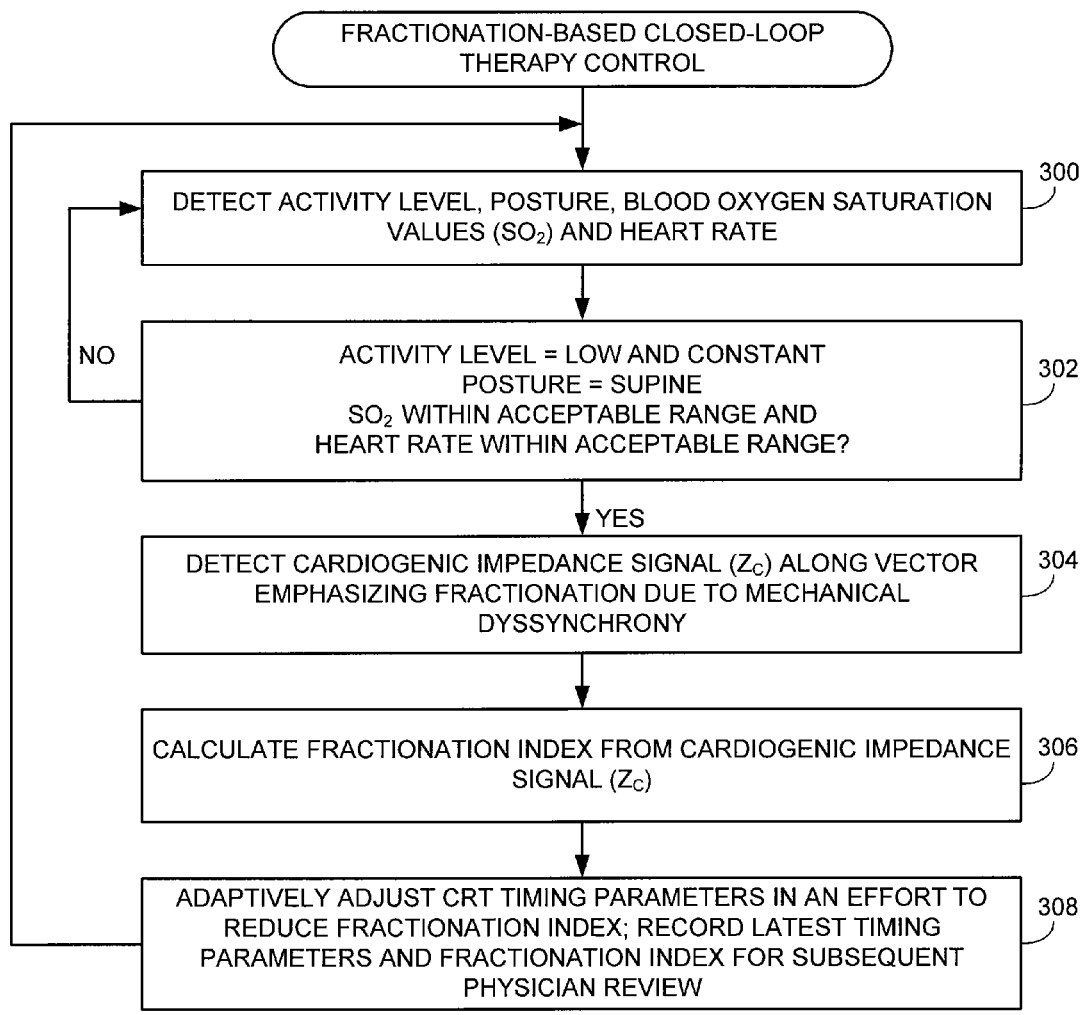
FIG. 6 is a flow diagram illustrating exemplary closed-loop technique for adaptively adjusting pacing timing parameters in accordance with the technique of FIG. 2 wherein the adjustments are performed based on fractionation of the cardiogenic impedance signal.

FIG. 6 illustrates an exemplary implementation wherein parameters are adaptively adjusted so as to reduce a fractionation index derived from a cardiogenic impedance signal. The adaptive adjustment is only performed under certain conditions. Beginning at step 300, the pacer/ICD detects detect patient activity level, patient posture, blood oxygen saturation values ($SO_2$) and heart rate. Patient activity may be detected using an accelerometer or other physical activity sensor mounted within the pacer/ICD itself or positioned elsewhere within the patient. Depending upon the implementation, the physical activity sensor may be employed in conjunction with an "activity variance" sensor, which monitors the activity sensor diurnally to detect the low variance in the measurement corresponding to a rest state. For a complete description of an activity variance sensor, see U.S. Pat. No. 5,476,483 to Bornzin et al., entitled "System and Method for Modulating the Base Rate during Sleep for a Rate-Responsive Cardiac Pacemaker". Techniques for detecting patient posture or changes in posture are set forth in U.S. patent application Ser. No. 10/329,233, of Koh et al., entitled "System and Method for Determining Patient Posture Based On 3-D Trajectory Using an Implantable Medical Device". Other techniques are set forth in U.S. Pat. No. 6,044,297 to Sheldon, et al. "Posture and Device Orientation and Calibration for Implantable Medical Devices". Techniques for detecting $SO_2$ are described in U.S. Pat. No. 5,676,141 to Hollub, entitled "Electronic Processor for Pulse Oximeters". Depending upon the particular application, either arterial $SO_2$ (i.e. $SaO_2$), or venous $SO_2$ (i.e. $SvO_2$), or both, may be detected and exploited. Heart rate may be derived from an IEGM.

At step 302, the pacer/ICD determines whether all of the following are true: (1) the patient is at rest and has been at rest for some predetermined amount of time, based on patient activity; (2) the posture is supine; (3) $SO_2$ is within an acceptable predetermined range consistent with patient rest; and (4) heart rate is within an acceptable predetermined range consistent with rest (such as a heart rate below 80 beats per minute (BPM)). If these conditions are met, the pacer/ICD proceeds to steps 304-308 to adaptively adjust the pacing parameters. That is, at step 304, the pacer/ICD detects at least one cardiogenic impedance signal $Z_C$ along a vector emphasizing fractionation due to mechanical dyssynchrony within the supine posture. In this regard, some sensing vectors are more sensitive to patient posture than others are. Accordingly, the pacer/ICD may be programmed to examine different cardiogenic impedance signals derived along different sensing vectors to identify the signal exhibiting the most fractionation within the supine posture. At step 306, the pacer/ICD calculates a fractionation index from the selected cardiogenic impedance signal $Z_C$ using any of the techniques discussed above, such as by counting notches within cardiogenic impedance signal or evaluating its frequency range. At step 308, the pacer/ICD adaptively adjusts CRT timing parameters in an effort to reduce the fractionation index and also records the latest timing parameters and fractionation index values for subsequent physician review.

Processing then returns to step 300 and, so long as the conditions of step 302 are still met, the pacer/ICD will continually and incrementally adjust the CRT parameters using the adaptive procedure. This helps ensure that adjustments are made while the patient is in a particular resting state so that changes to cardiogenic impedance due to factors other than the changes in the CRT parameters (such as patient activity) will not adversely affect the adaptive procedure. By looking at just the fractionation index, the procedure can typically be performed in real-time (though, as already noted, some lossy data compression may be appropriate to reduce the amount of data to be processed at any given time.) Once the patient becomes active again, further adaptive adjustments to CRT parameters are suspended until the patient is again at rest. Note that the list of patient status conditions in step 302 is merely exemplary. In other examples, more or fewer conditions may be used. For example, in other implementations, the patient need not necessarily be supine. Also, if the patient is subject to AF, the acceptable heart rate range may be expanded or that condition eliminated entirely so that frequent episodes of AF do not prevent adaptive adjustment of CRT parameters.

Figure 7:
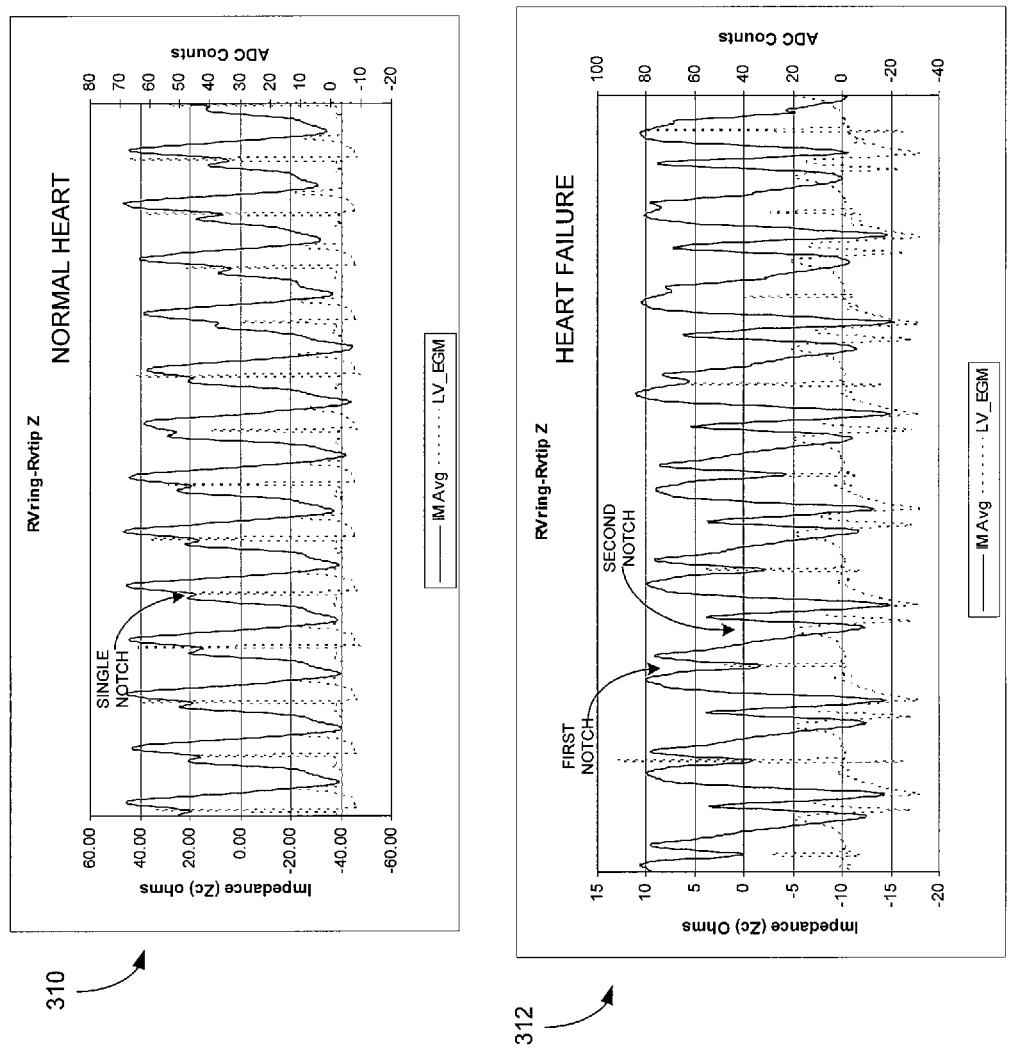
FIG. 7 is a graph illustrating exemplary cardiogenic impedance signals that may be processed in accordance with the technique of FIG. 6, and particularly illustrating the fractionation of the cardiogenic impedance signal exhibited during heart failure.

Fractionation of a cardiogenic impedance signal due to heart failure is illustrated with FIG. 7. A first graph 310 illustrates a cardiogenic impedance trace (solid line) and an IEGM trace (dotted line) for a patient without significant heart failure. The impedance trace (IM avg) was obtained via bipolar sensing RV tip to RV ring. The IEGM in an LV IEGM and is shown scaled according to "counts" from an analog to digital converter (ADC). A second graph 312 instead illustrates a cardiogenic impedance trace (solid line) and an IEGM trace (dotted line) for a patient with heart failure. As can be seen, within the normal heart trace 310, the portion of the cardiogenic impedance signal associated with each individual heart beat exhibits one notch. This single notch arises due to the uniform contraction of the RV and the LV and corresponds to the QRS complex of the IEGM. However, in the diseased heart of graph 312, an additional significant notch appears within the cardiogenic impedance trace within the time interval of the T-wave of the IEGM. This additional notch appears to occur due to a time delay between LV contraction and RV contraction and hence is indicative of mechanical dyssynchrony between the LV and RV associated with heart failure. The adaptive adjustment procedure of FIG. 7 is iteratively performed to identify CRT parameters (i.e. LV-RV time delay parameters) that reduce the degree of fractionation within the cardiogenic impedance waveform. Depending upon the patient, it may be possible to adaptively adjust the timing parameters so as to completely eliminate the second notch. In other cases, depth of the second notch is instead reduced.

Note that various other indices may be generated and exploited. For example, a "dyssynchrony index" can be calculated as: $DYS.IND = \Delta T_{RV} - \Delta T_{LV}$, where the $\Delta T$ for each ventricle represents the time delay of the notch in the T-wave of the IEGM with respect to the second notch of the cardiogenic impedance waveform. This delay is representative of the electromechanical delay of the respective ventricle. Additionally, the time delay between the occurrence of the QRS complex of the IEGM and the occurrence of a corresponding peak in the impedance waveform can be indicative of worsening association between the electrical and mechanical activities of the corresponding ventricle. Since the delay in the impedance peak reflects the electromechanical delay, the Dyssynchrony Index can be trended for purposes of monitoring and treating heart failure. In normal hearts, DYS.IND is typically less than 30 msecs. In heart failure patients, DYS.IND typically increases to 60-80 msecs, or higher. Thus, the DYS.IND value can be used to optimize LV-RV intervals for Bi-V pacing. In one implementation, the pacer/ICD applies a LV-RV delay (by stimulating the left ventricle first, then the right ventricle) that is approximately equal to the value of the DYS.IND. Adjustment of the LV-RV delay is preferably made in real time. The dyssynchrony index and other indices are discussed in the related applications, cited above.

Figure 8:
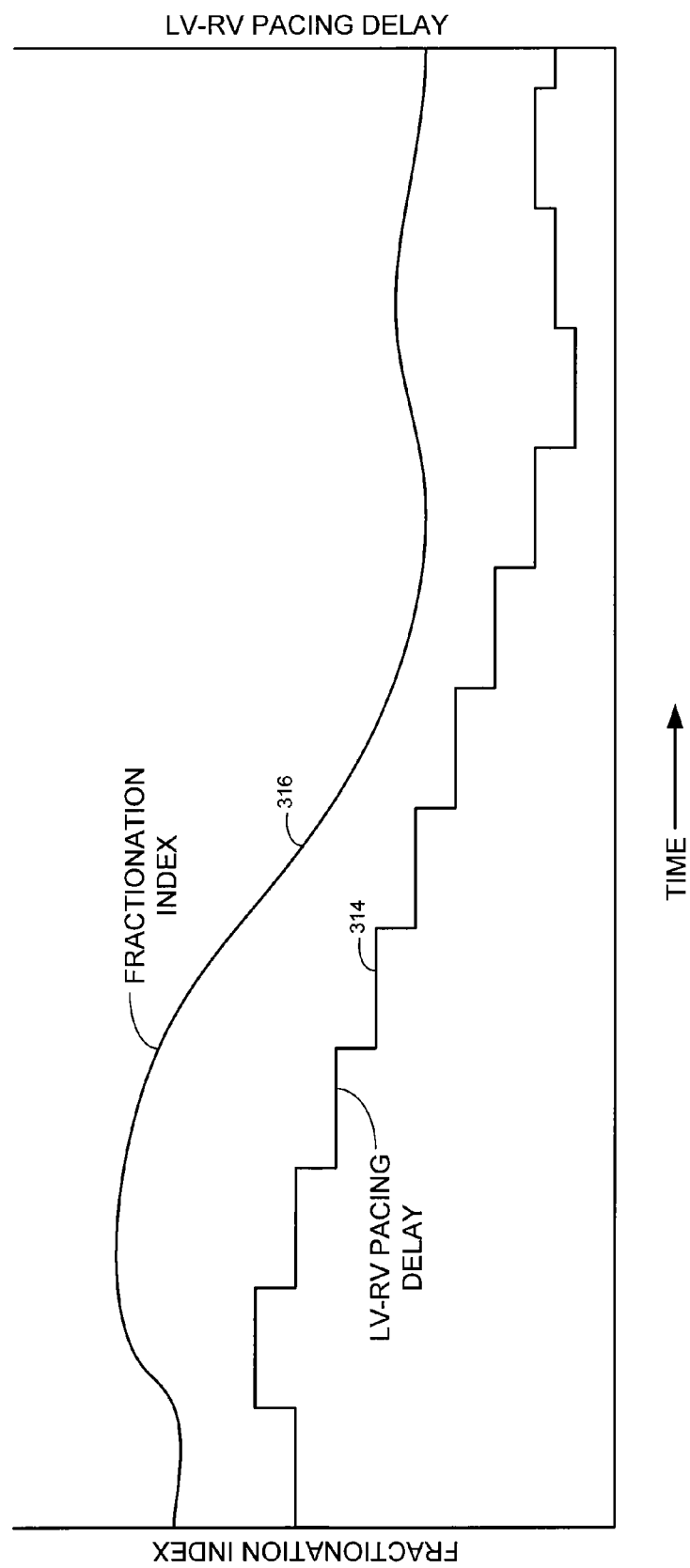
FIG. 8 is a stylized graph illustrating exemplary trends in a fractionation index derived from cardiogenic impedance signals that may be processed in accordance with the technique of FIG. 6, and particularly illustrating corresponding adjustments to LV-RV pacing delays.

FIG. 8 illustrates exemplary adaptive adjustment made to an LV-RV pacing delay in an effort to reduce a fractionation index. As can be seen, the pacer/ICD initially increases the LV-RV delay 314, shown on an arbitrary scale, in an effort to decrease the fractionation index 316, also shown on an arbitrary scale. (In the example shown, the fractionation index is a continuous variable, as might be obtained via frequency analysis of the cardiogenic impedance signal.) However, the fractionation index instead increases, indicating that the direction of change of the LV-RV delay was initially incorrect. Accordingly, the pacer/ICD begins decreasing the LV-RV delay, yielding a significant reduction in the fractionation index. Eventually further decreases cause the fractionation index to again increase. At that point, the pacer/ICD increases the LV-RV delay, this time using a smaller increment, and further adaptive adjustments are made using that smaller increment (or using still smaller increments) to optimize the LV-RV delay to a value achieving the lowest fractionation index.

Thus, FIGS. 6-8 specifically illustrate the use of fractionation index as a means for adaptively adjusting CRT parameters. As already explained, a wide variety of other parameters or indices can instead be exploited. The following three figures illustrate some such parameters.

Figure 9:
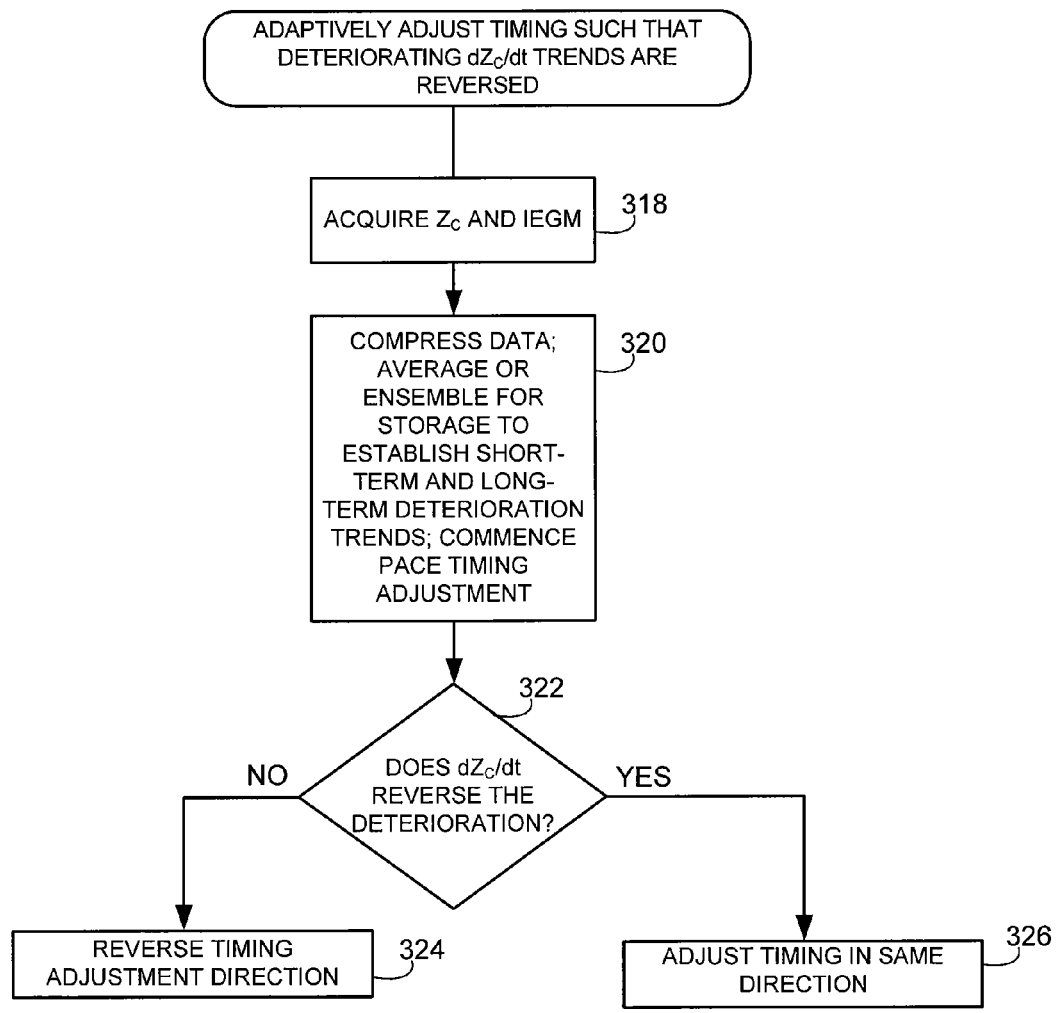
FIG. 9 is a flow diagram illustrating an exemplary $dZ_C/dt$-based adjustment technique that may be performed in accordance with the general technique of FIG. 2.

FIG. 9 illustrates adaptive adjustment based on $dZ_C/dt$ trends (i.e. trends in the rate of change of the cardiogenic impedance signal $Z_C$ over time). At step 318, the pacer/ICD acquires $Z_C$ and an IEGM signal. At step 320, the pacer/ICD compresses data using lossy compression; averages or ensemble averages the data for storage to establish short-term and long-term trends (such as deteriorating values of $dZ_C/dt$ (max)); and then commences pace timing adjustment, such as an incremental reduction in LV-RV delay. In this regard, the maximum value of $dZ_C/dt$ is indicative of systolic slope, i.e. contraction. (The minimum value of $dZ_C/dt$ is indicative of diastolic slope, i.e. relaxation.) A decrease in $dZ_C/dt$(max) generally indicates progression of heart failure. At step 322, the pacer/ICD then evaluates whether the $dZ_C/dt$ exhibits a reversal in deterioration. If so, then further adjustments are made in the same direction at step 324 (i.e. LV-RV delay is further decremented.) Otherwise, at step 326, the adjustment direction is changed (i.e. LV-RV delay is instead incremented.) Although not shown, processing then loops back for further adaptive adjustments to the pacing parameters in a closed-loop, as has already been explained. Also, although not shown, the pacer/ICD should verify that the lead system is functioning properly before acquiring $Z_C$ (or other signals.)

Figure 10:
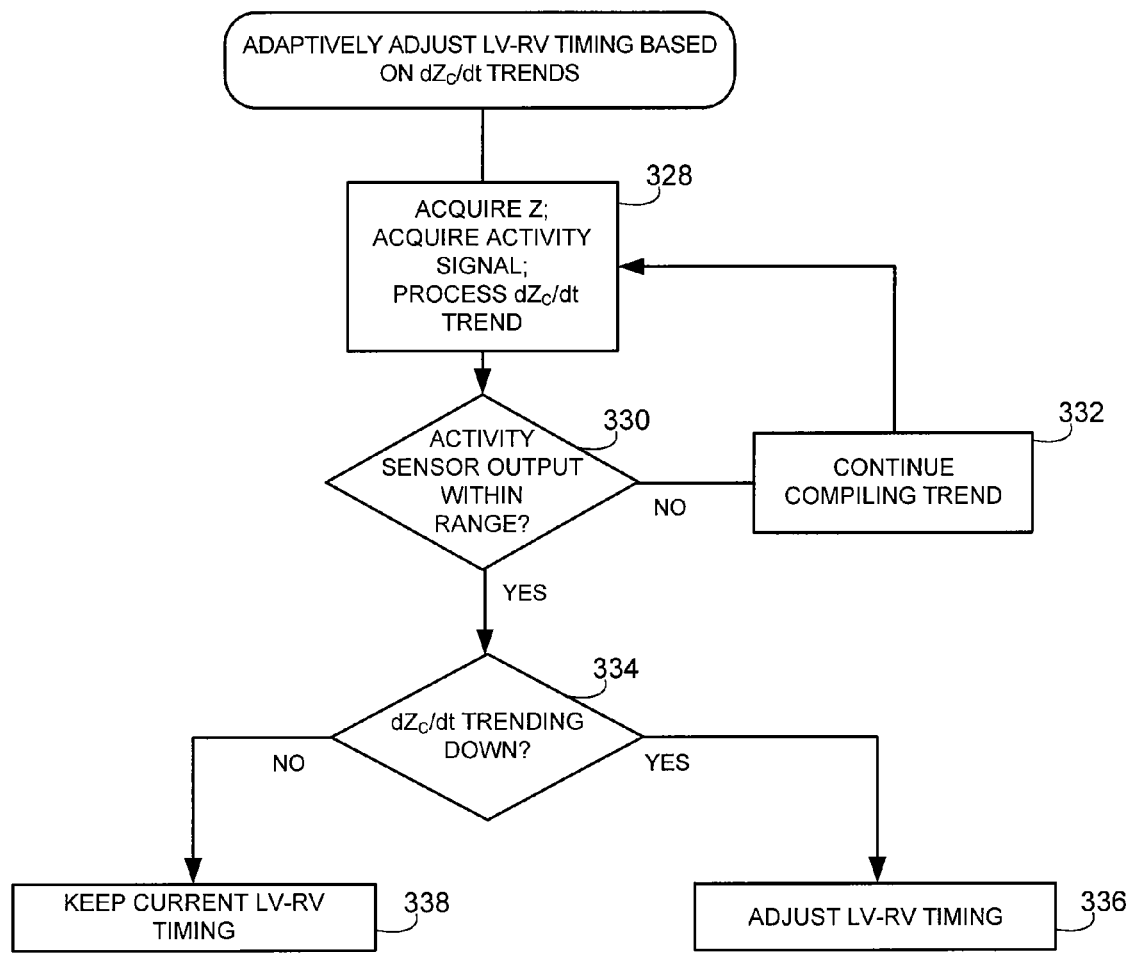
FIG. 10 is a flow diagram illustrating another exemplary $dZ_C/dt$-based adjustment technique that may be performed in accordance with the general technique of FIG. 2.

FIG. 10 illustrates another example where adaptive adjustment is based on $dZ_C/dt$ trends but where adjustments are only made if patient activity levels are in an acceptable range. At step 328, the pacer/ICD acquires $Z_C$ and an activity signal and processes any $dZ_C/dt$ trends. At step 330, the pacer/ICD then evaluates whether the activity sensor signal is within an acceptable range (typically set to indicate that the patient is at rest.) If not, the pacer/ICD simply continues compiling trends in $dZ_C/dt$, at step 332. If, however, the activity levels are within an acceptable range, the pacer/ICD then determines, at step 334, whether $dZ_C/dt$ is trending down (i.e. whether the $dZ_C/dt$ value indicate a deterioration of cardiac function). If so, the LV-RV pacing delay is adjusted, at step 336. If not, the LV-RV pacing delay is left unchanged, at step 338. Again, although not shown, processing then loops back for further adaptive adjustments to the pacing parameters in a closed-loop, as has already been explained.

Figure 11:
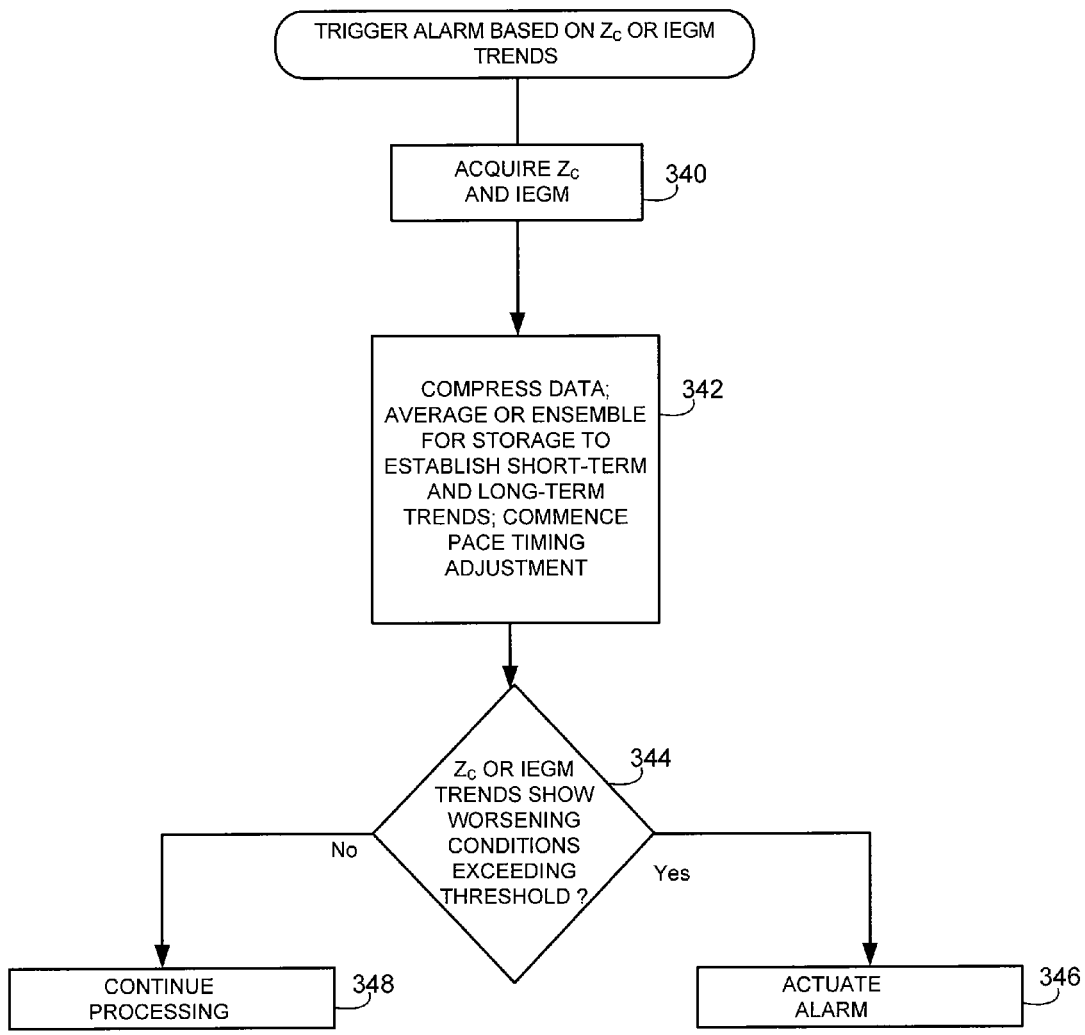
FIG. 11 is a flow diagram illustrating an exemplary technique fro triggering an alarm that may be performed in accordance with the general technique of FIG. 2.

FIG. 11 illustrates an example wherein an alarm is activated upon detection of significantly deteriorating trends. At step 340, the pacer/ICD acquires $Z_C$ and an IEGM signal. At step 342, the pacer/ICD compresses data; averages or ensemble averages the data for storage to establish short-term and long-term trends (such as deteriorating values of $dZ_C/dt$ (max)); and then commences pace timing adjustment, such as an incremental reduction in LV-RV delay. At step 344, the pacer/ICD then evaluates whether trends in $Z_C$ or in the IEGM exhibits worsening conditions and that the amount of deterioration exceeds a predetermined threshold. If so, then an alarm is activated, at step 346, such as the implantable alarm discussed above. Otherwise, at step 348, processing continues without alarm activation (by, e.g. looping back to the beginning to acquire new data.)

In some implementations, before the alarm is activated, the pacer/ICD employs at least one other detection technique to corroborate the detection of the deterioration of cardiac function. Techniques for detecting or tracking heart failure are set forth the following patents and patent applications: U.S. patent application Ser. No. 11/100,008, of Kil et al., entitled "System And Method For Detecting Heart Failure And Pulmonary Edema Based On Ventricular End-Diastolic Pressure Using An Implantable Medical Device", filed Apr. 5, 2005; U.S. patent application Ser. No. 11/014,276, of Min et al., entitled "System And Method For Predicting Heart Failure Based On Ventricular End-Diastolic Volume/Pressure Using An Implantable Medical Device", filed Dec. 15, 2004; U.S. patent application Ser. No. 10/810,437, of Bornzin et al., entitled "System and Method for Evaluating Heart Failure Based on Ventricular End-Diastolic Volume Using an Implantable Medical Device," filed Mar. 26, 2004 and U.S. patent application Ser. No. 10/346,809, of Min et al., entitled "System and Method for Monitoring Cardiac Function via Cardiac Sounds Using an Implantable Cardiac Stimulation Device," filed Jan. 17, 2003. See also: U.S. Pat. No. 6,572,557, to Tchou, et al., cited above. U.S. Pat. No. 6,645,153, to Kroll et al., entitled "System and Method for Evaluating Risk of Mortality Due To Congestive Heart Failure Using Physiologic Sensors", and U.S. Pat. No. 6,438,408 to Mulligan et al., entitled "Implantable Medical Device For Monitoring Congestive Heart Failure."

In addition to the various parameters/strategies discussed above, various "fiducial" points may be identified within the Z and IEGM signals and used to control therapy. For example, the delay between an R-wave of the IEGM and a $Z_C$ max point of the cardiogenic impedance signal $Z_C$ can reflect a worsening condition. For example, if the delay between IEGM and $Z_C$ fiducial points is too long, the A-V timing could be decreased. If the LV $Z_C$ fiducial points lag too much behind RV $Z_C$ fiducial points, the LV-RV timing could be decreased or adjusted appropriately. The adjustments preferably have the objective of minimizing the 'energy' (as defined in digital signal processing (DSP) concepts) of an error vector that defines the deviation from optimal or expected outputs. These analyses, whether that of fiducial points, or other parameters, are preferably based on trends. The trends can be computed short term (e.g. days, weeks) or long term (e.g. weeks, months). The trends preferably analyze ensemble parameters of signals from one or more leads. For example, to reduce or eliminate artifacts caused by patient activity levels or position, fiducial point timing and $Z_C$ data should be averaged over a sufficiently long interval. The interval could extend over a few days. Given that the storage of data spanning such long intervals might require significant on-chip memory, IEGM and $Z_C$ signals could be stored in a compressed format, as already explained. Lossy compression can be used as it is not expected to negatively affect the performance of the techniques, particularly lossy compression techniques that have the advantage of running real-time. Also, as already explained, information from other sensors can be used in the decision process. For example, in order to increase the accuracy, predictability or specificity of the control loop data from an accelerometer can be used to confirm that $Z_C$ values are processed at the same general level of patient activity. It is known that many hemodynamic parameters discussed above can vary with the activity level. Hence, it is advisable to correlate their analysis with activity indicators, such that consistent trends are revealed and activity artifacts are eliminated. Similarly, data from position, posture, pressure or $SO_2$ sensors are exploited. In addition to controlling the CRT pace timing, the fiducial point techniques described herein can also be used for preliminary diagnosis purposes, such as to trigger the aforementioned alarms for warning the patient and/or physician.

What have been described are various exemplary techniques for evaluating cardiac function using cardiogenic impedance signals and for adaptively adjusting pacing parameters in response thereto. Trends in cardiac function can also be detected based on the cardiogenic impedance signals. The techniques have been described with respect to examples wherein the implantable system performs the operations. However, principles of the invention are applicable to other systems. For example, trends in cardiac function can instead be detected using an external programmer or other external system based on cardiogenic impedance signals detected by the implanted device then transmitted to the external system. Moreover, although primarily described with respected to examples having a pacer/ICD, other implantable medical devices may be equipped to exploit the techniques described herein. For the sake of completeness, an exemplary pacer/ICD will now be described, which includes components for performing the functions and steps already described.

Exemplary Pacer/ICD

Figure 13:
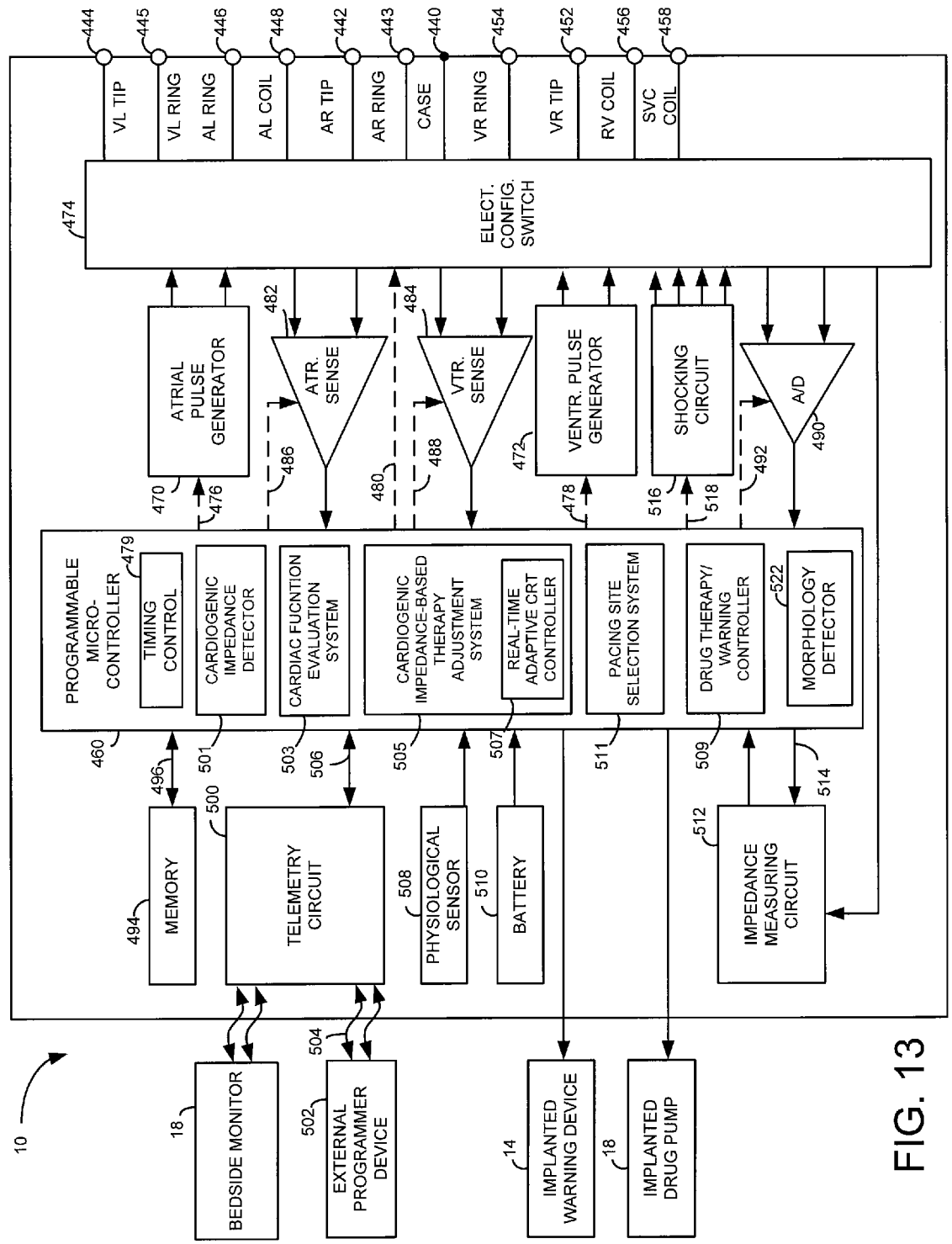
FIG. 13 a functional block diagram of the pacer/ICD of FIG. 12, illustrating basic circuit elements that provide cardioversion, defibrillation and/or pacing stimulation in the heart and particularly illustrating components for controlling CRT based on cardiogenic impedance.

With reference to FIGS. 12 and 13, a description of an exemplary pacer/ICD will now be provided. FIG. 12 provides a simplified block diagram of the pacer/ICD, which is a dual-chamber stimulation device capable of treating both fast and slow arrhythmias with stimulation therapy, including cardioversion, defibrillation, and pacing stimulation, and also capable of detecting and exploiting cardiogenic impedance signals. To provide other atrial chamber pacing stimulation and sensing, pacer/ICD 10 is shown in electrical communication with a heart 412 by way of a left atrial lead 420 having an atrial tip electrode 422 and an atrial ring electrode 423 implanted in the atrial appendage. Pacer/ICD 10 is also in electrical communication with the heart by way of a right ventricular lead 430 having, in this embodiment, a ventricular tip electrode 432, a right ventricular ring electrode 434, a right ventricular (RV) coil electrode 436, and a superior vena cava (SVC) coil electrode 438. Typically, the right ventricular lead 430 is transvenously inserted into the heart so as to place the RV coil electrode 436 in the right ventricular apex, and the SVC coil electrode 438 in the superior vena cava. Accordingly, the right ventricular lead is capable of receiving cardiac signals, and delivering stimulation in the form of pacing and shock therapy to the right ventricle.

Figure 14:
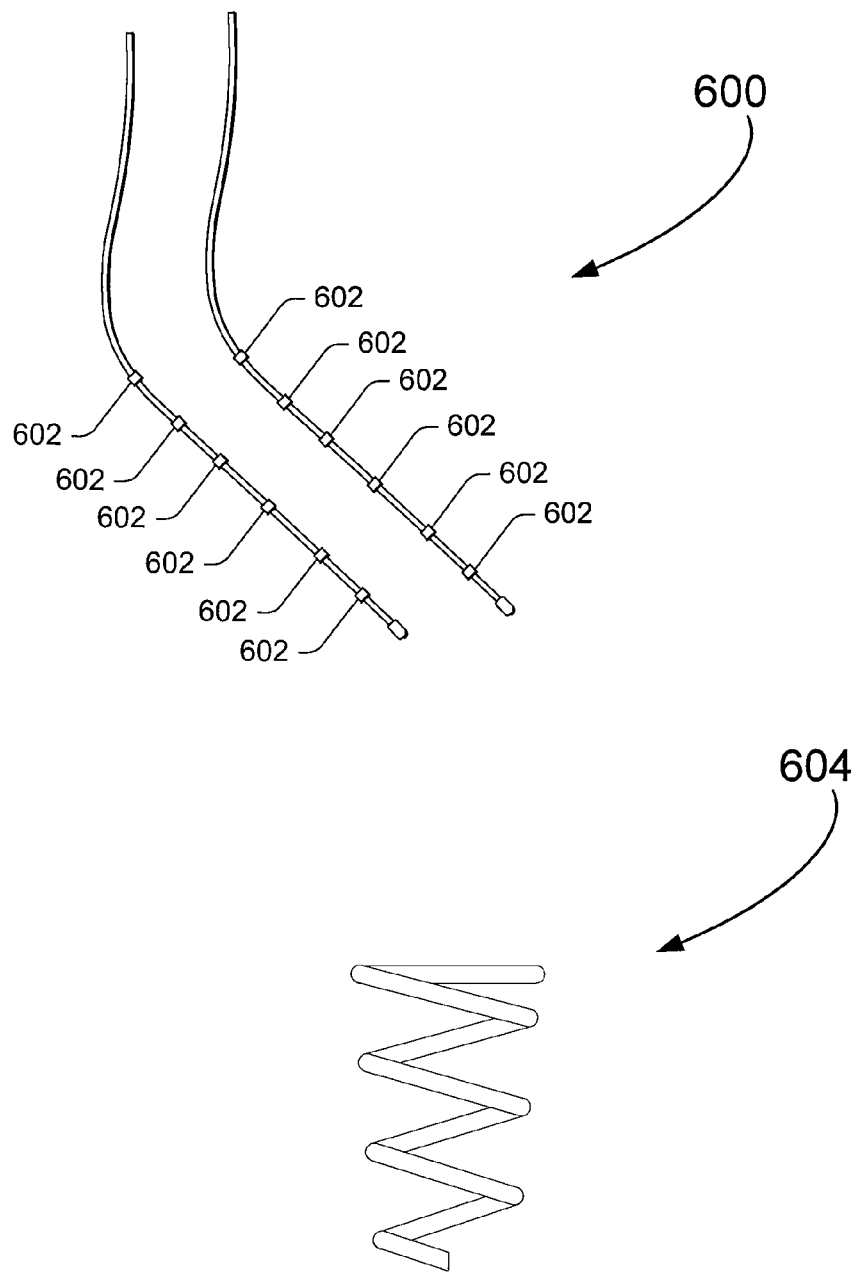
FIG. 14 illustrates alternative, exemplary lead designed that may be used in conjunction with the pacer/ICD of FIGS. 12 and 13.

To sense left atrial and ventricular cardiac signals and to provide left chamber pacing therapy, pacer/ICD 10 is coupled to a CS lead 424 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary CS lead 424 is designed to receive atrial and ventricular cardiac signals and to deliver left ventricular pacing therapy using at least a left ventricular tip electrode 426 and a LV ring electrode 425, left atrial pacing therapy using at least a left atrial ring electrode 427, and shocking therapy using at least a left atrial coil electrode 428. With this configuration, biventricular pacing can be performed. Although only three leads are shown in FIG. 12, it should also be understood that additional leads (with one or more pacing, sensing and/or shocking electrodes) might be used and/or additional electrodes might be provided on the leads already shown. Some alternative lead embodiments are illustrated in FIG. 14, discussed below.

A simplified block diagram of internal components of pacer/ICD 10 is shown in FIG. 13. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. The housing 440 for pacer/ICD 10, shown schematically in FIG. 13, is often referred to as the "can", "case" or "case electrode" and may be programmably selected to act as the return electrode for all "unipolar" modes. The housing 440 may further be used as a return electrode alone or in combination with one or more of the coil electrodes, 428, 436 and 438, for shocking purposes. The housing 440 further includes a connector (not shown) having a plurality of terminals, 442, 443, 444, 445, 446, 448, 452, 454, 456 and 458 (shown schematically and, for convenience, the names of the electrodes to which they are connected are shown next to the terminals). As such, to achieve right atrial sensing and pacing, the connector includes at least a right atrial tip terminal ($A_R$ TIP) 442 adapted for connection to the atrial tip electrode 422 and a right atrial ring ($A_R$ RING) electrode 443 adapted for connection to right atrial ring electrode 423. To achieve left chamber sensing, pacing and shocking, the connector includes at least a left ventricular tip terminal ($V_L$ TIP) 444, a left ventricular ring terminal ($V_L$ RING) 445, a left atrial ring terminal ($A_L$ RING) 446, and a left atrial shocking terminal ($A_L$ COIL) 448, which are adapted for connection to the left ventricular ring electrode 426, the left atrial ring electrode 427, and the left atrial coil electrode 428, respectively. To support right chamber sensing, pacing and shocking, the connector further includes a right ventricular tip terminal ($V_R$ TIP) 452, a right ventricular ring terminal ($V_R$ RING) 454, a right ventricular shocking terminal ($V_R$ COIL) 456, and an SVC shocking terminal (SVC COIL) 458, which are adapted for connection to the right ventricular tip electrode 432, right ventricular ring electrode 434, the $V_R$ coil electrode 436, and the SVC coil electrode 438, respectively.

At the core of pacer/ICD 10 is a programmable microcontroller 460, which controls the various modes of stimulation therapy. As is well known in the art, the microcontroller 460 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 460 includes the ability to process or monitor input signals (data) as controlled by a program code stored in a designated block of memory. The details of the design and operation of the microcontroller 460 are not critical to the invention. Rather, any suitable microcontroller 460 may be used that carries out the functions described herein. The use of microprocessor-based control circuits for performing timing and data analysis functions are well known in the art.

As shown in FIG. 13, an atrial pulse generator 470 and a ventricular pulse generator 472 generate pacing stimulation pulses for delivery by the right atrial lead 420, the right ventricular lead 430, and/or the CS lead 424 via an electrode configuration switch 474. It is understood that in order to provide stimulation therapy in each of the four chambers of the heart, the atrial and ventricular pulse generators, 470 and 472, may include dedicated, independent pulse generators, multiplexed pulse generators or shared pulse generators. The pulse generators, 470 and 472, are controlled by the microcontroller 460 via appropriate control signals, 476 and 478, respectively, to trigger or inhibit the stimulation pulses.

The microcontroller 460 further includes timing control circuitry (not separately shown) used to control the timing of such stimulation pulses (e.g., pacing rate, AV delay, atrial interconduction (inter-atrial) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 474 includes a plurality of switches for connecting the desired electrodes to the appropriate I/O circuits, thereby providing complete electrode programmability. Accordingly, the switch 474, in response to a control signal 480 from the microcontroller 460, determines the polarity of the stimulation pulses (e.g., unipolar, bipolar, combipolar, etc.) by selectively closing the appropriate combination of switches (not shown) as is known in the art.

Atrial sensing circuits 482 and ventricular sensing circuits 484 may also be selectively coupled to the right atrial lead 420, CS lead 424, and the right ventricular lead 430, through the switch 474 for detecting the presence of cardiac activity in each of the four chambers of the heart. Accordingly, the atrial (ATR. SENSE) and ventricular (VTR. SENSE) sensing circuits, 482 and 484, may include dedicated sense amplifiers, multiplexed amplifiers or shared amplifiers. The switch 474 determines the "sensing polarity" of the cardiac signal by selectively closing the appropriate switches, as is also known in the art. In this way, the clinician may program the sensing polarity independent of the stimulation polarity. Each sensing circuit, 482 and 484, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits, 482 and 484, are connected to the microcontroller 460 which, in turn, are able to trigger or inhibit the atrial and ventricular pulse generators, 470 and 472, respectively, in a demand fashion in response to the absence or presence of cardiac activity in the appropriate chambers of the heart.

For arrhythmia detection, pacer/ICD 10 utilizes the atrial and ventricular sensing circuits, 482 and 484, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., AS, VS, and depolarization signals associated with fibrillation which are sometimes referred to as "F-waves" or "Fib-waves") are then classified by the microcontroller 460 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 490. The data acquisition system 490 is configured to acquire intracardiac electrogram signals, convert the raw analog data into a digital signal, and store the digital signals for later processing and/or telemetric transmission to an external device 502. The data acquisition system 490 is coupled to the right atrial lead 420, the CS lead 424, and the right ventricular lead 430 through the switch 474 to sample cardiac signals across any pair of desired electrodes. The microcontroller 460 is further coupled to a memory 494 by a suitable data/address bus 496, wherein the programmable operating parameters used by the microcontroller 460 are stored and modified, as required, in order to customize the operation of pacer/ICD 10 to suit the needs of a particular patient. Such operating parameters define, for example, the amplitude or magnitude, pulse duration, electrode polarity, for both pacing pulses and impedance detection pulses as well as pacing rate, sensitivity, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 494 through a telemetry circuit 500 in telemetric communication with the external device 502, such as a programmer, transtelephonic transceiver or a diagnostic system analyzer. The telemetry circuit 500 is activated by the microcontroller by a control signal 506. The telemetry circuit 500 advantageously allows intracardiac electrograms and status information relating to the operation of pacer/ICD 10 (as contained in the microcontroller 460 or memory 494) to be sent to the external device 502 through an established communication link 504. Pacer/ICD 10 further includes an accelerometer or other physiologic sensor 508, commonly referred to as a "rate-responsive" sensor because it is typically used to adjust pacing stimulation rate according to the exercise state of the patient. However, the physiological sensor 508 may further be used to detect changes in cardiac output, changes in the physiological condition of the heart, or diurnal changes in activity (e.g., detecting sleep and wake states) and to detect arousal from sleep. Accordingly, the microcontroller 460 responds by adjusting the various pacing parameters (such as rate, AV delay, V-V delay, etc.) at which the atrial and ventricular pulse generators, 470 and 472, generate stimulation pulses. While shown as being included within pacer/ICD 10, it is to be understood that the physiologic sensor 508 may also be external to pacer/ICD 10, yet still be implanted within or carried by the patient. A common type of rate responsive sensor is an activity sensor incorporating an accelerometer or a piezoelectric crystal, which is mounted within the housing 440 of pacer/ICD 10. Other types of physiologic sensors are also known, for example, sensors that sense the oxygen content of blood, respiration rate and/or minute ventilation, pH of blood, ventricular gradient, etc.

The pacer/ICD additionally includes a battery 510, which provides operating power to all of the circuits shown in FIG.

6. The battery 510 may vary depending on the capabilities of pacer/ICD 10. If the system only provides low voltage therapy, a lithium iodine or lithium copper fluoride cell typically may be utilized. For pacer/ICD 10, which employs shocking therapy, the battery 510 should be capable of operating at low current drains for long periods, and then be capable of providing high-current pulses (for capacitor charging) when the patient requires a shock pulse. The battery 510 should also have a predictable discharge characteristic so that elective replacement time can be detected. Accordingly, appropriate batteries are employed.

As further shown in FIG. 13, pacer/ICD 10 is shown as having an impedance measuring circuit 512 which is enabled by the microcontroller 460 via a control signal 514. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. The impedance measuring circuit 120 is advantageously coupled to the switch 74 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 460 further controls a shocking circuit 516 by way of a control signal 518. The shocking circuit 516 generates shocking pulses of low (up to 0.5 joules), moderate (0.5-10 joules) or high energy (11 to 40 joules), as controlled by the microcontroller 460. Such shocking pulses are applied to the heart of the patient through at least two shocking electrodes, and as shown in this embodiment, selected from the left atrial coil electrode 428, the RV coil electrode 436, and/or the SVC coil electrode 438. The housing 440 may act as an active electrode in combination with the RV electrode 436, or as part of a split electrical vector using the SVC coil electrode 438 or the left atrial coil electrode 428 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 460 is capable of controlling the synchronous or asynchronous delivery of the shocking pulses.

Insofar as cardiogenic impedance is concerned, the microcontroller includes a cardiogenic impedance $Z_C$ detector 501 operative to detect cardiogenic impedance $Z_C$ as discussed above and a cardiogenic impedance-based therapy adjustment system 503 operative to adjust therapy provided by the device based on the cardiogenic impedance signal $Z_C$, also as discussed above. As already explained, therapy may be adjusted so as to improve cardiac function. Accordingly, a cardiac function measurement system 505 is provided, which is operative to derive a measure of cardiac function from the cardiogenic impedance signal $Z_C$. As one of its components, the cardiogenic impedance-based therapy adjustment system 503 may include a real-time adaptive CRT controller 507 operative to adaptively adjust CRT parameters based on the cardiogenic impedance signal $Z_C$. Diagnostic data pertaining to cardiogenic impedance is stored in memory 494. Warning and/or notification signals are generated, when appropriate, by a warning controller 509 then relayed to the bedside monitor 18 via telemetry system 500 or to external programmer 502. Controller 509 can also controller an implantable drug pump, if one is provided, to deliver appropriate medications. Terminals for connecting the implanted warning device and the implanted drug pump to the pacer/ICD are not separately shown. A pacing site selection system 511 is provided to selectively adjust pacing sites using techniques to be described below in FIG. 15.

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, using application specific integrated circuits (ASICs) or the like.

Turning now to FIG. 14, some alternative lead implementations are illustrated, which may be used in connection with the pacer/ICD of FIG. 13. A first lead system 600, includes multiple electrodes 602 per lead to permit sensing of multiple cardiogenic impedance signals, either lead to lead or between two electrode of the same lead. Multiple leads per chamber, such as multiple RV leads, may be used. To sense cardiogenic impedance, ring electrodes a preferred, i.e. electrode of about the same size and shape as otherwise conventional ring electrodes within current leads systems, though tip-sized or coil-sized electrodes might also be used. For bipolar sensing, the electrodes of the sensing pair are preferably at least one inch apart. A second lead 604 shown in FIG. 14 has a helical shape, with greater diameter at its proximal end, to accommodate more electrodes (not individually shown within FIG. 14) within a given heart chamber. With multiple electrodes per lead, the pacer/ICD can select particular combinations of leads for use in delivering pacing therapy (such as CRT) so as to improve the measure of cardiac function as determined based on cardiogenic impedance.

Figure 15:
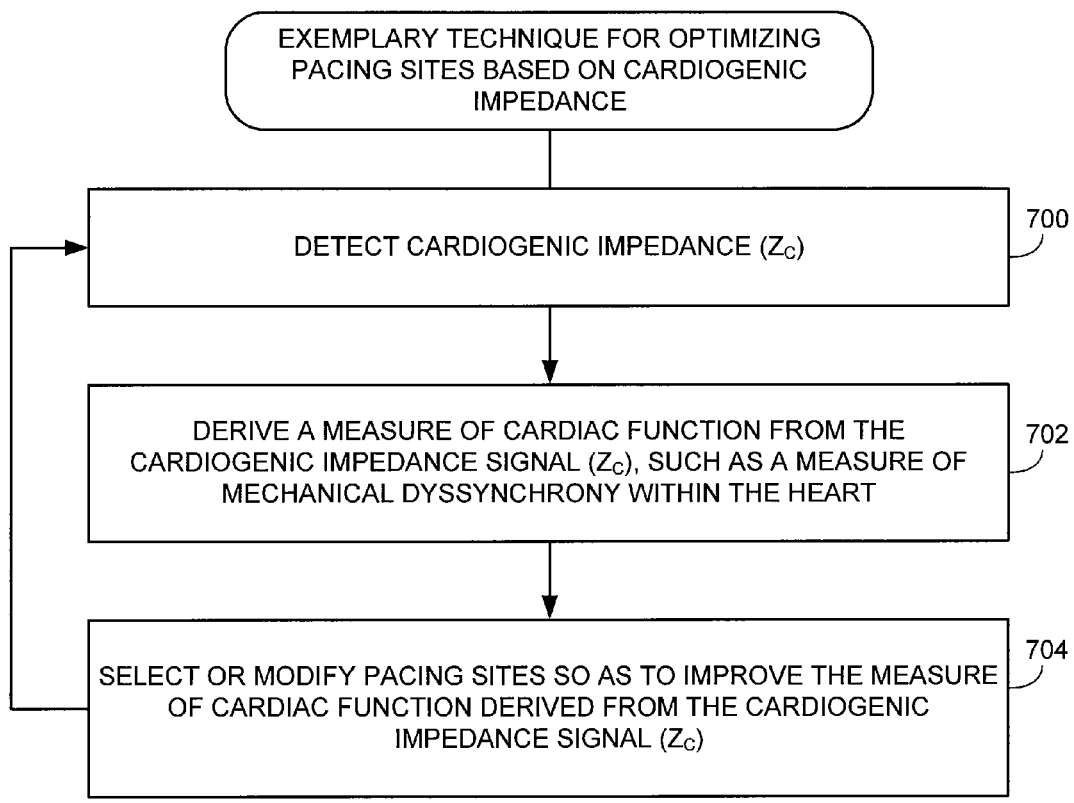
FIG. 15 illustrates a technique for selecting optimal pacing sites for CRT based on cardiogenic impedance.

FIG. 15 summarizes techniques for selecting or modifying particular pacing sites based on cardiogenic impedance. Briefly, at steps 700 and 702, the pacer/ICD detects cardiogenic impedance ($Z_C$) and derives at least one measure of cardiac function, as discussed above. Then, at step 704, the pacer/ICD selects or modifies pacing sites so as to improve the measure of cardiac function. For example, the pacer/ICD might select CRT pacing sites so as to improve one or more of: fractionation, cardiac pressure, mechanical dyssynchrony, electrical dyssynchrony, cardiac performance, blood oxygen saturation, contractility, peak-to-peak amplitudes, and changes in cardiogenic impedance with time (dZ/dt). These parameters are discussed above. In one particular example, the pacer/ICD is equipped with N electrodes in the RV, where N is an arbitrary number of electrodes. The pacer/ICD evaluates the degree of fractionation arising when unipolar pacing is performed using each RV electrode, i.e. $RV_1$-case, $RV_2$-case, $RV_3$-case, etc. The pacer/ICD then selects the particular RV electrode that achieves the least amount of fractionation of the cardiogenic impedance signal for use in performing further pacing. Once optimal pacing sites are chose, CRT timing parameters may be optimized using the techniques above for use with that particular pacing site. Similarly, the LV lead may carry multiple CRT pacing electrodes. In a similar fashion, optimal pacing configurations can be selected from the electrodes on the LV CRT lead. Yet similarly, combined RV and LV pacing configurations could be selected to optimize patient parameters, such as those listed above. Alternatively, all these pacing electrodes can be separately, or individually, distributed on endocardial, epicardial or within myocardial tissue. The electrodes can be carried on separate leads, on multiple leads or implanted individually.

In general, while the invention has been described with reference to particular embodiments, modifications can be made thereto without departing from the spirit and scope of the invention. Note also that the term "including" as used herein is intended to be inclusive, i.e. "including but not limited to".

What is claimed is:

1. A method for controlling therapy provided by an implantable cardiac stimulation device to reduce mechanical dyssynchrony, the method comprising:
   detecting an interventricular cardiogenic impedance signal ($Z_C$) associated with individual heartbeats with the interventricular cardiogenic impedance signal having an interventricular waveform morphology, the interventricular cardiogenic impedance signal having sufficient resolution to detect a notch within an individual heartbeat occurring even in the absence of mechanical dyssynchrony, the interventricular waveform morphology of individual heartbeats having additional features corresponding to periods of time when chambers of the heart are not beating uniformly due to mechanical dyssynchrony;
   deriving a measure of interventricular fractionation from the interventricular waveform morphology, wherein interventricular fractionation quantifies the features of the interventricular waveform morphology of individual heartbeats corresponding to periods of time when chambers of the heart are not beating uniformly due to mechanical dyssynchrony; and
   adjusting therapy provided by the device based on the interventricular cardiogenic impedance signal ($Z_C$) to improve the measure of interventricular fractionation and reduce periods of time when chambers of the heart are not beating uniformly due to mechanical dyssynchrony;
   wherein the features of the interventricular waveform morphology corresponding to periods of time when chambers of the heart are not beating uniformly due to mechanical dyssynchrony include a plurality of additional notches within an individual heartbeat arising due to mechanical dyssynchrony and wherein therapy is adjusted to reduce at least one of the plurality of additional notches within the individual heartbeat to reduce interventricular fractionation and reduce mechanical dyssynchrony.

2. The method of claim 1 wherein detecting an interventricular cardiogenic impedance signal ($Z_C$) includes:
   measuring a raw impedance signal ($Z_0$) along at least one sensing vector passing through at least a portion of both ventricles of the heart of a patient in which the device is implanted; and
   extracting the interventricular cardiogenic impedance signal ($Z_C$) from the raw impedance signal ($Z_0$), wherein the cardiogenic impedance signal ($Z_C$) is representative of variations in impedance due to the beating of the heart of the patient including the beating of both ventricles.

3. The method of claim 2 wherein extracting the cardiogenic impedance signal ($Z_C$) from the raw impedance signal ($Z_0$) includes extracting a signal representative of a change in $Z_C$ with respect to time ($dZ_C/dt$) and wherein the measure of interventricular fractionation is derived from the signal representative of a change in $Z_C$ with respect to time.

4. The method of claim 2 wherein extracting the cardiogenic impedance signal ($Z_C$) from the raw impedance signal ($Z_0$) includes extracting a signal representative of a difference between maximum and minimum cardiogenic impedance values ($Z_{C\text{-}max}$-$Z_{C\text{-}max}$) and wherein the measure of interventricular fractionation is derived from the signal representative of a difference between maximum and minimum cardiogenic impedance values.

5. The method of claim 1 further including storing the cardiogenic impedance signal ($Z_C$) using signal compression.

6. The method of claim 5 wherein signal compression is achieved by selectively storing cardiogenic impedance values within histogram bins.

7. The method of claim 1 wherein separate interventricular cardiogenic impedance signals are detected along separate sensing vectors passing through at least a portion of both ventricles of the heart of the patient and wherein separate measures of interventricular fractionation are derived from the separate interventricular cardiogenic impedance signals and wherein therapy is adjusted based on a combination of the separate measures of interventricular fractionation.

8. The method of claim 7 wherein multiple impedance sensing electrodes are provided along at least one ventricular lead and wherein the separate cardiogenic impedance signals are derived using the multiple electrodes of the at least one ventricular lead in combination with at least one electrode of at least one other lead.

9. The method of claim 7 wherein multiple impedance sensing electrodes are provided along a plurality of ventricular leads and wherein the separate cardiogenic impedance signals are derived using the electrodes of the plurality of ventricular leads.

10. The method of claim 1 further including identifying trends in changes in interventricular fractionation.

11. The method of claim 10 wherein deriving a value representative of cardiac pressure includes deriving a value representative of one or more of left atrial pressure (LAP) and left ventricular end diastolic pressure ($LV_{END}$).

12. The method of claim 1 further including deriving a value representative of cardiac pressure from the cardiogenic impedance signal ($Z_C$) and wherein therapy is adjusted to improve both the value representative of cardiac pressure derived from the cardiogenic impedance signal ($Z_C$) and the measure of interventricular fractionation.

13. The method of claim 1 further including detecting an intracardiac electrogram (IEGM) signal and deriving a measure of electrical dyssynchrony from the intracardiac electrogram (IEGM) signal and wherein therapy is adjusted to improve both the measure of electrical dyssynchrony and the measure of interventricular fractionation.

14. The method of claim 1 further including detecting a significant deterioration in the measure of interventricular fractionation.

15. The method of claim 14 further including activating a warning device in response to detection of a significant deterioration in the measure of interventricular fractionation.

16. The method of claim 1 further including deriving a value representative of cardiac pressure from a cardiac pressure sensor and wherein therapy is adjusted to improve both the measure of cardiac pressure derived from the cardiac pressure sensor and the measure of interventricular fractionation.

17. The method of claim 1 wherein adjusting therapy provided by the device is performed in a closed loop based on repeatedly updated measures of interventricular fractionation.

18. The method of claim 1 wherein therapy is adjusted by adjusting one or more pacing timing parameters.

19. The method of claim 18 wherein therapy is adjusted by adjusting an atrioventricular (AV) timing parameter.

20. The method of claim 18 wherein therapy is adjusted by adjusting an inter-ventricular (LV-RV) timing parameter.

21. The method of claim 18 wherein therapy is adjusted by adjusting an intra-ventricular ($LV_1$-$LV_2$, $RV_1$-$RV_2$) timing parameter.

22. The method of claim 18 wherein pacing timing parameters are adjusted to reduce one or more of: inter-ventricular mechanical dyssynchrony (LV-RV); intra-ventricular mechanical dyssynchrony ($LV_1$-$LV_1$, $LV_1$-$LV_1$); inter-ventricular electrical dyssynchrony (LV-RV); intra-ventricular electrical dyssynchrony ($LV_1$-$LV_1$, $LV_1$-$LV_1$); inter-atrial mechanical dyssynchrony (LV-RV); intra-atrial mechanical dyssynchrony ($LV_1$-$LV_1$, $LV_1$-$LV_1$); inter-atrial electrical dyssynchrony (LV-RV); intra-atrial electrical dyssynchrony ($LV_1$-$LV_1$, $LV_1$-$LV_1$); and a fractionation index.

23. The method of claim 18 wherein pacing timing parameters are adjusted to improve one or more of left atrial pressure (LAP), $LV_{END}$ pressure, stroke volume, cardiac output, $SO_2$, and cardiac contractility.

24. The method of claim 1 wherein therapy is adjusted based on cardiogenic impedance signals detected only during particular patient activity levels as determined in conjunction with an activity sensor.

25. The method of claim 1 wherein therapy is adjusted based on cardiogenic impedance signals detected only while the patient is in a particular posture as determined in conjunction with a position sensor.

26. The method of claim 1 wherein therapy is adjusted based on cardiogenic impedance signals detected only while the patient has a particular blood oxygen saturation level as determined in conjunction with a blood oxygen saturation sensor.

27. The method of claim 1 wherein therapy is adjusted substantially in real-time.

28. The method of claim 1 wherein the device is equipped to selectively deliver pacing at any of a plurality of pacing sites and wherein the step of adjusting therapy based on the interventricular cardiogenic impedance signal ($Z_C$) is performed to select particular ventricular pacing sites based on the cardiogenic impedance signal ($Z_C$) to improve cardiac performance by reducing interventricular fractionation.

29. The method of claim 1 wherein the device is equipped to selectively deliver pacing at any of a plurality of pacing sites and wherein the ventricular pacing sites are selected so as to improve the measure of interventricular fractionation.

30. The method of claim 29 wherein ventricular pacing sites are selected so as to additionally improve one or more of: cardiac pressure, electrical dyssynchrony, cardiac performance, blood oxygen saturation, contractility, peak to peak amplitudes, and changes in cardiogenic impedance with time (dZ/dt).

31. The method of claim 1 wherein adjusting therapy includes:
detecting patient activity level, patient posture, blood oxygen saturation values ($SO_2$) and heart rate;
determining whether the patient is at rest and has been at rest for some predetermined amount of time, the posture is supine, $SO_2$ is within an acceptable predetermined range, and heart rate is within an acceptable predetermined range; and
if so, detecting at least one cardiogenic impedance signal $Z_C$ along a vector emphasizing interventricular fractionation due to mechanical dyssynchrony within the supine posture, calculating the number of notches from a selected cardiogenic impedance signal $Z_C$, and adjusting timing parameters to reduce the number of notches.

32. The method of claim 1 wherein adjusting therapy includes adjusting a therapeutic stimulation control parameter in a given direction and then detecting and evaluating whether a time rate of change in the interventricular cardiogenic impedance signal ($dZ_C/dt$) exhibits a reversal in deterioration and, if so, performing further adjustments in the same direction and, if not, reversing the adjustment direction to reduce periods of time when chambers of the heart are not beating uniformly due to mechanical dyssynchrony.

33. The method of claim 1 wherein detecting an interventricular cardiogenic impedance signal ($Z_C$) includes:
acquiring an activity signal along with $Z_C$;
detecting $dZ_C/dt$ and compiling trends in $dZ_C/dt$; and
evaluating whether the activity signal is within an acceptable range and, if so, determining whether $dZ_C/dt$ indicates a deterioration of interventricular fractionation; and wherein the step of adjusting therapy provided by the device is performed in response to an indication of deterioration of interventricular fractionation.

34. The method of claim 1 wherein the features of the interventricular waveform morphology corresponding to periods of time when chambers of the heart are not beating uniformly include higher spectral frequencies compared to spectral frequencies associated with periods of time when chambers of the heart are beating uniformly and wherein deriving a measure of interventricular fractionation includes deriving a measure of the higher spectral frequencies and wherein therapy is also adjusted to reduce the measure of the higher spectral frequencies to reduce interventricular fractionation.

35. The method of claim 1 wherein therapy is adjusted to reduce a number of notches within the individual heartbeat to reduce interventricular fractionation.

36. A system for controlling therapy provided by an implantable cardiac stimulation device to reduce the system comprising:
a cardiogenic impedance ($Z_C$) detector operative to detect an interventricular cardiogenic impedance signal ($Z_C$) associated with individual heartbeats, the interventricular cardiogenic impedance signal having an interventricular waveform morphology, the interventricular cardiogenic impedance signal having sufficient resolution to detect a notch within an individual heartbeat occurring even in the absence of mechanical dyssynchrony, the interventricular waveform morphology of individual heartbeats having additional features corresponding to periods of time when chambers of the heart are not beating uniformly due to mechanical dyssynchrony;
a cardiac function evaluation system operative to derive a measure of interventricular fractionation from the interventricular waveform morphology, wherein interventricular fractionation quantifies the features of the interventricular waveform morphology of individual heartbeats corresponding to the periods of time when chambers of the heart are not beating uniformly due to mechanical dyssynchrony; and
a cardiogenic impedance-based therapy adjustment system operative to adjust therapy provided by the device based on the interventricular cardiogenic impedance signal ($Z_C$) to improve the measure of interventricular fractionation and reduce periods of time when chambers of the heart are not beating uniformly due to mechanical dyssynchrony;

wherein the features of the interventricular waveform morphology corresponding to periods of time when chambers of the heart are not beating uniformly due to mechanical dyssynchrony include a plurality of additional notches within an individual heartbeat arising due to mechanical dyssynchrony and wherein the therapy adjustment system operates to adjust therapy to reduce at least one of the plurality of additional notches within the individual heartbeat to reduce interventricular fractionation and reduce mechanical dyssynchrony.

37. The system of claim 36 wherein the cardiogenic impedance-based therapy adjustment system includes a real-time adaptive cardiac resynchronization therapy (CRT) controller operative to adaptively adjust CRT parameters based on the cardiogenic impedance signal ($Z_C$) to improve the measure of interventricular fractionation.

38. The system of claim 36 wherein the device is equipped to selectively deliver pacing at any of a plurality of ventricular pacing sites and wherein the device further includes a pacing site selection system operative to select particular ventricular pacing sites based on the cardiogenic impedance signal ($Z_C$).

39. The system of claim 36 in an implantable cardiac stimulation device having at least one lead having a proximal end for connection to the implantable cardiac stimulation device and an opposing distal end, wherein the lead between its distal and proximal ends is helical with a decreasing radius of curvature from the proximal end to the distal end.

40. A system for controlling therapy provided by an implantable cardiac stimulation device to reduce mechanical dyssynchrony, the system comprising:
   means for detecting an interventricular cardiogenic impedance signal ($Z_C$) associated with individual heartbeats, the interventricular cardiogenic impedance signal having an interventricular waveform morphology, the interventricular cardiogenic impedance signal having sufficient resolution to detect a notch within an individual heartbeat occurring even in the absence of mechanical dyssynchrony, the interventricular waveform morphology of individual heartbeats having additional features corresponding to periods of time when chambers of the heart are not beating uniformly due to mechanical dyssynchrony;
   means for deriving a measure of interventricular fractionation from the interventricular waveform morphology, wherein interventricular fractionation quantifies the features of the interventricular waveform morphology of individual heartbeats corresponding to periods of time when chambers of the heart are not beating uniformly due to mechanical dyssynchrony; and
   means for adjusting therapy provided by the device based on the interventricular cardiogenic impedance signal ($Z_C$) so as to improve the measure of interventricular fractionation and reduce periods of time when chambers of the heart are not beating uniformly due to mechanical dyssynchrony;
   wherein the features of the interventricular waveform morphology corresponding to periods of time when chambers of the heart are not beating uniformly due to mechanical dyssynchrony include a plurality of additional notches within an individual heartbeat arising due to mechanical dyssynchrony and wherein the means for adjusting therapy operates to adjust therapy to reduce at least one of the plurality of additional notches within the individual heartbeat to reduce interventricular fractionation and reduce mechanical dyssynchrony.

41. A method for controlling therapy provided by an implantable cardiac stimulation device, the method comprising:
   detecting an interventricular cardiogenic impedance signal ($Z_C$) associated with individual heartbeats with the interventricular cardiogenic impedance signal having an interventricular waveform morphology, the interventricular waveform morphology of individual heartbeats having features corresponding to periods of time when chambers of the heart are not beating uniformly due to mechanical dyssynchrony;
   deriving a measure of interventricular fractionation from the interventricular waveform morphology, wherein interventricular fractionation quantifies the features of the interventricular waveform morphology of individual heartbeats corresponding to the periods of time when chambers of the heart are not beating uniformly due to mechanical dyssynchrony;
   adjusting therapy provided by the device based on the interventricular cardiogenic impedance signal ($Z_C$) to improve the measure of interventricular fractionation and reduce periods of time when chambers of the heart are not beating uniformly due to mechanical dyssynchrony; and
   wherein the features of the interventricular waveform morphology corresponding to periods of time when chambers of the heart are not beating uniformly due to mechanical dyssynchrony include higher spectral frequencies compared to spectral frequencies associated with periods of time when chambers of the heart are beating uniformly and wherein therapy is adjusted to reduce at least some of the higher spectral frequencies to reduce interventricular fractionation.

42. The method of claim 41 wherein separate interventricular cardiogenic impedance signals are detected along separate sensing vectors passing through at least a portion of both ventricles of the heart of the patient and wherein separate measures of interventricular fractionation are derived from the separate interventricular cardiogenic impedance signals and wherein therapy is adjusted based on a combination of the separate measures of interventricular fractionation.

43. The method of claim 41 further including identifying trends in changes in interventricular fractionation.

44. The method of claim 41 further including detecting an intracardiac electrogram (IEGM) signal and deriving a measure of electrical dyssynchrony from the intracardiac electrogram (IEGM) signal and wherein therapy is adjusted to improve both the measure of electrical dyssynchrony and the measure of interventricular fractionation.

45. The method of claim 41 further including detecting a significant deterioration in the measure of interventricular fractionation.

46. The method of claim 45 further including activating a warning device in response to detection of a significant deterioration in the measure of interventricular fractionation.

47. The method of claim 41 wherein adjusting therapy provided by the device is performed in a closed loop based on repeatedly updated measures of interventricular fractionation.

48. The method of claim 41 wherein the device is equipped to selectively deliver pacing at any of a plurality of pacing sites and wherein the ventricular pacing sites are selected so as to improve the measure of interventricular fractionation.

49. The method of claim 41 wherein detecting an interventricular cardiogenic impedance signal ($Z_C$) includes:
   acquiring an activity signal along with $Z_C$;
   detecting $dZ_C/dt$ and compiling trends in $dZ_C/dt$; and evaluating whether the activity signal is within an acceptable range and, if so, determining whether $dZ_C/dt$ indicates a deterioration of interventricular fractionation; and wherein the step of adjusting therapy provided by the device is performed in response to an indication of deterioration of interventricular fractionation.

50. A system for controlling therapy provided by an implantable cardiac stimulation device, the system comprising:
- a cardiogenic impedance ($Z_C$) detector operative to detect an interventricular cardiogenic impedance signal ($Z_C$) associated with individual heartbeats, the interventricular cardiogenic impedance signal having an interventricular waveform morphology, the interventricular waveform morphology of individual heartbeats having features corresponding to periods of time when chambers of the heart are not beating uniformly due to mechanical dyssynchrony;
- a cardiac function evaluation system operative to derive a measure of interventricular fractionation from the interventricular waveform morphology, wherein interventricular fractionation quantifies the features of the interventricular waveform morphology of individual heartbeats corresponding to the periods of time when chambers of the heart are not beating uniformly due to mechanical dyssynchrony; and
- a cardiogenic impedance-based therapy adjustment system operative to adjust therapy provided by the device based on the interventricular cardiogenic impedance signal ($Z_C$) to improve the measure of interventricular fractionation and reduce periods of time when chambers of the heart are not beating uniformly due to mechanical dyssynchrony;

wherein the features of the interventricular waveform morphology corresponding to periods of time when chambers of the heart are not beating uniformly due to mechanical dyssynchrony include higher spectral frequencies compared to spectral frequencies associated with periods of time when chambers of the heart are beating uniformly and wherein the therapy adjustment system operates to adjust therapy to reduce at least some of the higher spectral frequencies to reduce interventricular fractionation.

\* \* \* \* \*